US009884107B2

(12) United States Patent
Chackerian et al.

(10) Patent No.: US 9,884,107 B2
(45) Date of Patent: *Feb. 6, 2018

(54) **IMMUNOGENIC RESPIRATORY SYNCYTIAL VIRUS GL

(56) References Cited

OTHER PUBLICATIONS

Chackerian B, Briglio L, Albert PS, Lowy DR, Schiller JT. Induction of autoantibodies to CCR5 in macaques and subsequent effects upon challenge with an R5-tropic simian/human immunodeficiency virus. J Virol, 2004;78:4037-4047.

Chackerian B, Durfee MR, Schiller JT. Virus-like display of a neo-self antigen reverses B cell anergy in a B cell receptor transgenic mouse model. J Immunol, 2008;180:5816-5825.

Chackerian B, Lowy DR, Schiller JT. Conjugation of a self-antigen to papillomavirus-like particles allows for efficient induction of protective autoantibodies. J Clin Invest, 2001;108:415-423.

Chackerian B, Lovvy DR, Schiller JT. Induction of autoantibodies to mouse CCR5 with recombinant papillomavirus particles. Proc. Natl. Acad. Sci, 1999;96:2373-2378.

Chackerian B, Rangel M, Hunter Z, Peabody DS. Virus and virus-like particle-based immunogens for Alzheimer's disease induce antibody responses against amyloid-beta without concomitant T cell responses. Vaccine, 2006;24:6321-6331.

Cornuz J, Zwahlen S, Jungi WF, et al. A vaccine against nicotine for smoking cessation: a randomized controlled trial. PLoS One, 2008;3:e2547.

Dintzis HM, Dintzis RZ, Vogelstein B. Molecular determinants of immunogenicity: the immunon model of immune response. Proc Natl Acad Sci, 1976;73:3671-3675.

Dintzis RZ, Middleton MH, Dintzis HM. Inhibition of anti-DNP antibody formation by high doses of DNP-polyacrylamide molecules; effects of hapten density and hapten valence. J Immunol, 1985;135:423-427.

Ekiert DC, Bhabha G, Elsliger MA, Friesen RH, Jongeneelen M, Throsby M, Goudsmit J, Wilson IA. Antibody recognition of a highly conserved influenza virus epitope. Science, 2009;324:246-251.

Fehr T, Skrastina D, Pumpens P, Zinkernagel RM. T cell-independent type I antibody response against B cell epitopes expressed repetitively on recombinant virus particles. Proc Natl Acad Sci, 1998;95:9477-9481.

Feldman SA, Hendry RM, Beeler JA. Identification of a linear heparin binding domain for human respiratory syncytial virus attachment glycoprotein G. J Virol, 1999;73:6610-6617.

Hall CB, Walsh EE, Long CE, Schnabel KC. Immunity to and frequency of reinfection with respiratory syncytial virus. J Infect Dis, 1991;163:693-698.

Harro CD, Pang YY, Roden RB, et al. Safety and immunogenicity trial in adult volunteers of a human papillomavirus 16 L1 virus-like particle vaccine. J Natl Cancer Inst, 2001;93:284-292.

Law M, Maruyama T, Lewis J, et al. Broadly neutralizing antibodies protect against hepatitis C virus quasispecies challenge. Nat Med, 2008;14:25-27.

Li Q, Cao C, Chackerian B, Schiller J, Gordon M, Ugen KF, Morgan D. Overcoming antigen masking of anti-amyloidbeta antibodies reveals breaking of B cell tolerance by virus-like particles in amyloidbeta immunized amyloid precursor protein transgenic mice. BMC Neurosci, 2004;5:21.

Lim F, Peabody DS. RNA recognition site of PP7 coat protein. Nucleic Acids Res, 2002;30:4138-4144.

Lopez JA, Bustos R, Orvell C, Berois M, Arbiza J, Garcia-Barreno B, Melero JA. Antigenic structure of human respiratory syncytial virus fusion glycoprotein. J Virol, 1998;72:6922-6928.

Naelero JA, Garcia-Barreno B, Martinez I, Pringle CR, Cane PA. Antigenic structure, evolution and immunobiology of human respiratory syncytial virus attachment (G) protein. J Gen Virol, 1997;78(Pt10):2411-2418.

Milich DR, Chen M, Schodel F, Peterson DL, Jones JF, Hughes JL Role of B cells in antigen presentation of the hepatitis B core. Proc Natl Acad Sci, 1997;94:14648-14653.

Olmsted RA, Elango N, Prince GA, Murphy BR, Johnson PR, Moss B, Chanock RM, Collins PL. Expression of the F glycoprotein of respiratory syncytial virus by a recombinant vaccinia virus: comparison of the individual contributions of the F and G glycoproteins to host immunity. Proc Natl Acad Sci, 1986;83:7462-7466.

Olson MR, Varga SM. Pulmonary immunity and immunopathology: lessons from respiratory syncytial virus. Expert Rev Vaccines, 2008;7:1239-1255.

Peabody DS. Translational repression by bacteriophage MS2 coat protein expressed from a plasmid. A system for genetic analysis of a protein-RNA interaction. J Biol Chem, 1990;265:5684-5689.

Peabody DS, Lim F. Complementation of RNA binding site mutations in MS2 coat protein heterodimers. Nucleic Acids Res, 1996;24:2352-2359.

Peabody DS, Manifold-Wheeler B, Medford A, Jordan SK, Caldeira JC, Chackerian B. Immunogenic display of diverse peptides on virus-like particles of RNA phage MS2. J Mol Biol, 2008;380:252-263.

Stott EH, Taylor G, Ball LA, Anderson K, Young KK, King AM, Wertz GW. Immune and histopathological responses in animals vaccinated with recombinant vaccinia viruses that express individual genes of human respiratory syncytial virus. J Virol, 1987;61:3855-3861.

Sui J, Hwang S, Perez G, et al. Structural and functional bases for broad-spectrum neutralization of avian and human influenza A viruses. Nat Struct Mol Biol, 2009;16:265-273.

Tars K, Fridborg K, Bundule M, Liljas L. The three-dimensional structure of bacteriophage PP7 from Pseudomonas aeruginosa at 3.7-A resolution. Virology, 2000;272:331-337.

Thyagarajan R, Arunkumar N, Song W. Polyvalent antigens stabilize B cell antigen receptor surface signaling microdomains. J Immunol, 2003;170:6099-6106.

Tissot AC, Maurer P, Nussberger J, et al. Effect of immunisation against angiotensin II with CYT006-AngQb on ambulatory blood pressure: a double-blind, randomised, placebo-controlled phase IIa study. Lancet, 2008;371:821-827.

Zhang LF, Zhou J, Chen LL, Cai QY, Bao QY, Zheng FY, Lu JQ, Padmanabha J, Hengst K, Malcolm K, Frazer IH. HPV6b virus like particles are potent immunogens without adjuvant in man. Vaccine 2000;18:1051-1058.

Bastien, et al. Protective Immune Responses Induced by the Immunization of Mice with a Recombinant Bacteriophage Displaying an Epitope of the Human Respiratory Syncytial Virus. Virology, 1997;234:118-122.

* cited by examiner

FIGURE 1

Nucleotide and amino acid sequences of the AB-loop of wild-type PP7 and MS2 coat protein and the RSV recombinants.

A. RSV target sequences:

RSV F protein "Synagis" epitope (amino acids 252-278) SEQ ID NO: 5

L T N S E L L S L I N D M P I T N D Q K K L M S N N V

RSV G protein target region (amino acids 164-197) SEQ ID. NO: 20

CACTTCGAAGTTTTCAACTTCGTTCCGTGCTCTATCTGCTCTAACAACCCGACCTGCTGGGCTATCTGC
AAACGTATCCCGAACAAAAAACCGGGTAAAAAA
H F E V F N F V P C S I C S N N P T C W A I C K R I P N K K P G K K (SEQ ID NO:38)

B. Sequences of the downstream copy of coat protein.

p2P7K32 (PP7) (*KpnI site in italics*) SEQ ID NO: 21

1 2 3 4 5 6 7 8 9 10 11 12 13 14 15 16 17 18
ATGGCCAAAACCATCGTTCTTTCGGTC*GGTACC*GCTACTCGCACTCTGACTGAG
M A K T I V L S V G T A T R T L T E (SEQ ID NO:39)

pDSP1 (MS2) (*SalI site in italics*) SEQ ID NO: 22

1 2 3 4 5 6 7 8 9 10 11 12 13 14 15 16 17
GCTAACTTTACTCAGTTCGTTCTC*GTCGAC*AATGGCGGTACCGGCGACGTG
A N F T Q F V L V D N G G T G D V (SEQ ID NO:40)

C. Specific F peptide insertions were constructed using the following primers (only MS2 primers are shown here).

FIGURE 1 (CONT'D)

*(Restriction site in italics,* insertion in bold*)*:

S10.1 SEQ ID NO: 23

GTTCTC*GTCGAC*AATGGCCTGACCAACTCTGAACTGCTGTCTCTGATCGGCGACGTGACT
GTCGCC

V L V D N G L T N S E L L S L I G D V T V A (SEQ ID NO:41)

S10.2 SEQ ID NO: 24

GTTCTC*GTCGAC*AATGGCTCTGAACTGCTGTCTCTGATCAACGACATGGGCGACGTGACT
GTCGCC

V L V D N G S E L L S L I N D M G D V T V A (SEQ ID NO:42)

S10.3 SEQ ID NO: 25

GTTCTC*GTCGAC*AATGGCCTGTCTCTGATCAACGACATGCCGATCACCGGCGACGTGACT
GTCGCC

V L V D N G L S L I N D M P I T G D V T V A (SEQ ID NO:43)

S10.4 SEQ ID NO: 26

GTTCTC*GTCGAC*AATGGCATCAACGACATGCCGATCACCAACGACCAGGGCGACGTGACT
GTCGCC

V L V D N G I N D M P I T N D Q G D V T V A (SEQ ID NO:44)

S10.5 SEQ ID NO: 27

GTTCTC*GTCGAC*AATGGCATGCCGATCACCAACGACCAGAAAAAACTGGGCGACGTGACT
GTCGCC

V L V D N G M P I T N D Q K K L G D V T V A (SEQ ID NO:45)

S10.6 SEQ ID NO: 28

GTTCTC*GTCGAC*AATGGCACCAACGACCAGAAAAAACTGATGTCTAACGGCGACGTGACT
GTCGCC

V L V D N G T N D Q K K L M S N G D V T V A (SEQ ID NO:46)

FIGURE 1 (CONT'D)

S10.7 SEQ ID NO: 29

GTTCTC*GTCGAC*AATGGCGACCAGAAAAAACTGATGTCTAACAACGTTGGCGACGTGACT
GTCGCC

V L V D N G D Q K K L M S N N V G D V T V A (SEQ ID NO:47)

D. Specific G peptide insertions were constructed using the following primers (only MS2 primers are shown here).

SEQ ID NO: 30

CACTTCGAAGTTTTCAACTTCGTTCCGTGCTCTATCTGCTCTAACAACCCGACCTGCTGGGCTATCTGC
AAACGTATCCCGAACAAAAAACCGGGTAAAAAA

H F E V F N F V P C S I C S N N P T C W A I C K R I P N K K P G K K (SEQ ID NO:48)

G16 SEQ ID NO: 31

GTTCTC*GTCGAC*AATGGCCCGTGCTCTATCTGCTCTAACAACCCGACCTGCTGGGCTATC
TGCAAAGGCGACGTGACTGTCGCC

V L V D N G P C S I C S N N P T C W A I C K G D V T V A (SEQ ID NO:49)

G14 SEQ ID NO: 32

GTTCTC*GTCGAC*AATGGCTGCTCTATCTGCTCTAACAACCCGACCTGCTGGGCTATCTGC
GGCGACGTGACTGTCGCC

V L V D N G C S I C S N N P T C W A I C G D V T V A (SEQ ID NO:50)

G12 SEQ ID NO: 33

GTTCTC*GTCGAC*AATGGCTCTATCTGCTCTAACAACCCGACCTGCTGGGCTATCGGCGAC
GTGACTGTCGCC

V L V D N G S I C S N N P T C W A I G D V T V A (SEQ ID NO:51)

G7 SEQ ID NO: 34

GTTCTC*GTCGAC*AATGGCTGCTCTAACAACCCGACCTGCGGCGACGTGACTGTCGCC

V L V D N G C S N N P T C G D V T V A (SEQ ID NO:52)

FIGURE 1 (CONT'D)

G5 SEQ ID NO: 35

GTTCTC*GTCGAC*AATGGCTCTAACAACCCGACCGGCGACGTGACTGTCGCC

V L V D N G S N N P T G D V T V A  (SEQ ID NO:53)

Figure 2. Immune responses to recombinant MS2 VLPs displaying RSV peptides.
A. Antibody titers measured against a peptide representing the F antigen epitope.
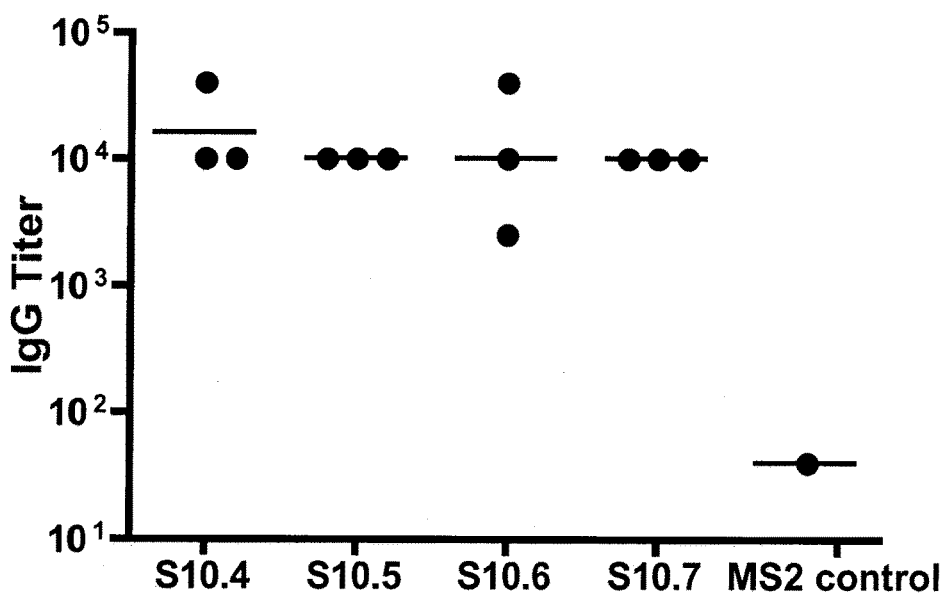
B. Antibody responses measured against recombinant F antigen
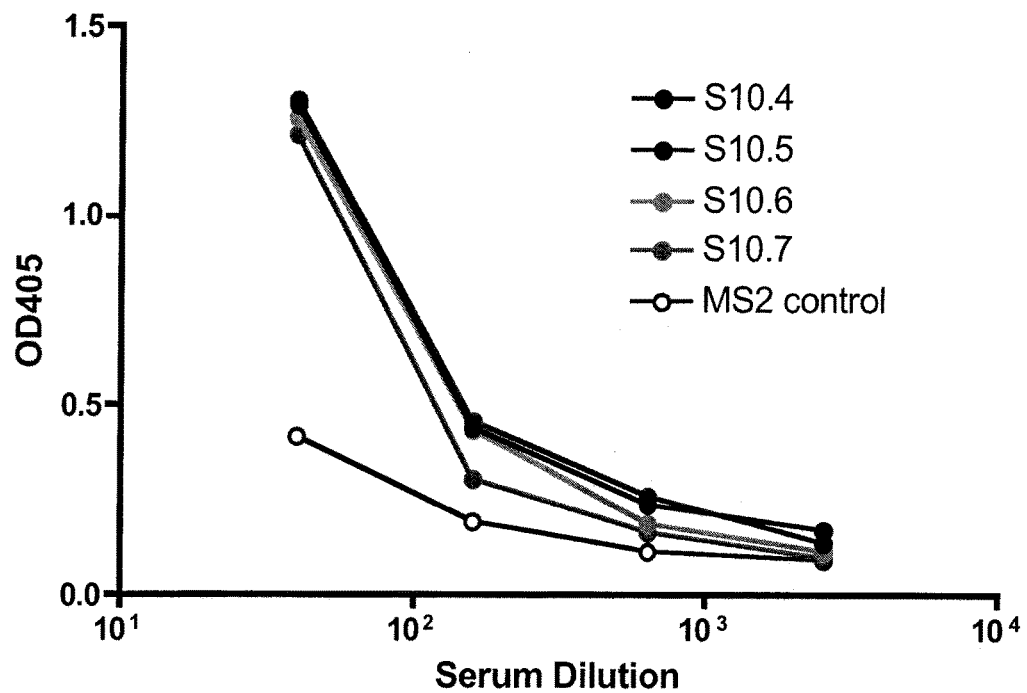

C. Antibody responses measured against inactivated RSV virions.

D. Antibody responses measured against inactivated RSV virions.

Figure 3. The pDSP1 plasmid.
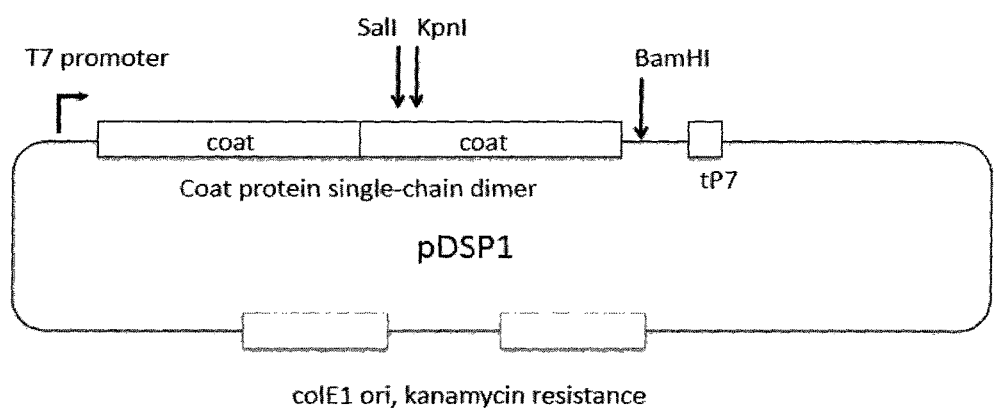

FIGURE 4

Nucleotide Sequence:

pDSP1 (SEQ ID NO: 1):

TTCTTAGAAAAACTCATCGAGCATCAAATGAAACTGCAATTTATTCATATCAGGATTATCAA
TACCATATTTTTGAAAAAGCCGTTTCTGTAATGAAGGAGAAAACTCACCGAGGCAGTTCCAT
AGGATGGCAAGATCCTGGTATCGGTCTGCGATTCCGACTCGTCCAACATCAATACAACCTAT
TAATTTCCCCTCGTCAAAAATAAGGTTATCAAGTGAGAAATCACCATGAGTGACGACTGAAT
CCGGTGAGAATGGCAAAAGCTTATGCATTTCTTTCCAGACTTGTTCAACAGGCCAGCCATTA
CGCTCGTCATCAAAATCACTCGCATCAACCAAACCGTTATTCATTCGTGATTGCGCCTGAGC
GAGACGAAATACGCGATCGCTGTTAAAAGGACAATTACAAACAGGAATCGAATGCAACCG
GCGCAGGAACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGGAGTACGG
ATAAAATGCTTGATGGTCGGAAGAGGCATAAATTCCGTCAGCCAGTTTAGTCTGACCATCTC
ATCTGTAACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGCCCATTTA
TACCCATATAAATCAGCATCCATGTTGGAATTTAATCGCGGCCTCGAGCAAGACGTTTCCCG
TTGAATATGGCTCATAACACCCCTTGTATTACTGTTTATGTAAGCAGACAGTTTTATTGTTCA
TGACCAAAATCCCTTAACGTGAGTTTTCGTTCCACTGAGCGTCAGACCCCGTAGAAAAGATC
AAAGGATCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCGAAGGTAA
CTGGCTTCAGCAGAGCGCAGATACCAAATACTGTCCTTCTAGTGTAGCCGTAGTTAGGCCAC
CACTTCAAGAACTCTGTAGCACCGCCTACATACCTCGCTCTGCTAATCCTGTTACCAGTGGC
TGCTGCCAGTGGCGATAAGTCGTGTCTTACCGGGTTGGACTCAAGACGATAGTTACCGGATA
AGGCGCAGCGGTCGGGCTGAACGGGGGGTTCGTGCACACAGCCCAGCTTGGAGCGAACGAC
CTACACCGAACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGCACGAGGGAG
CTTCCAGGGGGAAACGCCTGGTATCTTTATAGTCCTGTCGGGTTTCGCCACCTCTGACTTGA
GCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGA
ACGACCGAGCGCAGCGAGTCAGTGAGCGAGGAAGCGGAAGAGCGCCTGATGCGGTATTTTC
TCCTTACGCATCTGTGCGGTATTTCACACCGCATATATGGTGCACTCTCAGTACAATCTGCTC
TGATGCCGCATAGTTAAGCCAGTATACACTCCGCTATCGCTACGTGACTGGGTCATGGCTGC
GCCCCGACACCCGCCAACACCCGCTGACGCGCCCTGACGGGCTTGTCTGCTCCCGGCATCCG
CTTACAGACAAGCTGTGACCGTCTCCGGGAGCTGCATGTGTCAGAGGTTTTCACCGTCATCA

FIGURE 4 (CONT'D)

CCGAAACGCGCGAGGCAGCTGCGGTAAAGCTCATCAGCGTGGTCGTGAAGCGATTCACAGA
TGTCTGCCTGTTCATCCGCGTCCAGCTCGTTGAGTTTCTCCAGAAGCGTTAATGTCTGGCTTC
TGATAAAGCGGGCCATGTTAAGGGCGGTTTTTTCCTGTTTGGTCACTGAT
GCCTCCGTGTAAGGGGGATTTCTGTTCATGGGGGTAATGATACCGATGAAACGAGAGAGGA
TGCTCACGATACGGGTTACTGATGATGAACATGCCCGGTTACTGGAACGTTGTGAGGGTAA
ACAACTGGCGGTATGGATGCGGCGGGACCAGAGAAAAATCACTCAGGGTCAATGCCAGCGC
TTCGTTAATACAGATGTAGGTGTTCCACAGGGTAGCCAGCAGCATCCTGCGATGCAGATCCG
GAACATAATGGTGCAGGGCGCTGACTTCCGCGTTTCCAGACTTTACGAAACACGGAAACCG
AAGACCATTCATGTTGTTGCTCAGGTCGCAGACGTTTTGCAGCAGCAGTCGCTTCACGTTCG
CTCGCGTATCGGTGATTCATTCTGCTAACCAGTAAGGCAACCCCGCCAGCCTAGCCGGGTCC
TCAACGACAGGAGCACGATCATGCGCACCCGTGGCCAGGACCCAACGCTGCCCGAGATGCG
CCGCGTGCGGCTGCTGGAGATGGCGGACGCGATGGATATGTTCTGCCAAGGGTTGGTTTGC
GCATTCACAGTTCTCCGCAAGAATTGATTGGCTCCAATTCTTGGAGTGGTGAATCCGTTAGC
GAGGTGCCGCCGGCTTCCATTCAGGTCGAGGTGGCCCGGCTCCATGCACCGCGACGCAACG
CGGGGAGGCAGACAAGGTATAGGGCGGCGCCTACAATCCATGCCAACCCGTTCCATGTGCT
CGCCGAGGCGGCATAAATCGCCGTGACGATCAGCGGTCCAGTGATCGAAGTTAGGCTGGTA
AGAGCCGCGAGCGATCCTTGAAGCTGTCCCTGATGGTCGTCATCTACCTGCCTGGACAGCAT
GGCCTGCAACGCGGGCATCCCGATGCCGCCGGAAGCGAGAAGAATCATAATGGGGAAGGC
CATCCAGCCTCGCGTCGCGAACGCCAGCAAGACGTAGCCCAGCGCGTCGGCCGCCATGCCG
GCGATAATGGCCTGCTTCTCGCCGAAACGTTTGGTGGCGGGACCAGTGACGAAGGCTTGAG
CGAGGGCGTGCAAGATTCCGAATACCGCAAGCGACAGGCCGATCATCGTCGCGCTCCAGCG
AAAGCGGTCCTCGCCGAAAATGACCCAGAGCGCTGCCGGCACCTGTCCTACGAGTTGCATG
ATAAAGAAGACAGTCATAAGTGCGGCGACGATAGTCATGCCCCGCGCCCACCGGAAGGAGC
TGACTGGGTTGAAGGCTCTCAAGGGCATCGGCTCTCCCTTATGCGACTCCTGCATTAGGAAG
CAGCCCAGTAGTAGGTTGAGGCCGTTGAGCACCGCCGCCGCAAGGAATGGTGCATGCAAGG
AGATGGCGCCCAACAGTCCCCGGCCACGGGGCCTGCCACCATACCCACGCCGAAACAAGC
GCTCATGAGCCCGAAGTGGCGAGCCCGATCTTCCCCATCGGTGATGTCGGCGATATAGGCG
CCAGCAACCGCACCTGTGGCGCCGGTGATGCCGGCCACGATGCGTCCGGCGTAGAGGATCG
AGATCTCGATCCCGCGAAATTAATACGACTCACTATAGGGAGACCACAACGGTTTCCCTCTA
GAAATAATTTTGTTTAACTTTAAGAAGGAGATATACCATGGCTTCTAACTTTACTCAGTTCGT
TCTCGTTGACAATGGCGGAACTGGCGACGTGACTGTCGCCCCAAGCAACTTCGCTAACGGG
GTCGCTGAATGGATCAGCTCTAACTCGCGTTCACAGGCTTACAAAGTAACCTGTAGCGTTCG
TCAGAGCTCTGCGCAGAATCGCAAATACACCATCAAAGTCGAGGTGCCTAAAGTGGCAACC
CAGACTGTTGGTGGTGTAGAGCTTCCTGTAGCCGCATGGCGTTCGTACTTAAATATGGAACT
AACCATTCCAATTTTCGCTACGAATTCCGACTGCGAGCTTATTGTTAAGGCAATGCAAGGTC

FIGURE 4 (CONT'D)

TCCTAAAAGATGGAAACCCGATTCCCTCAGCAATCGCAGCAAACTCCGGCCTCTACGGCAA
CTTTACTCAGTTCGTTCTCGTCGACAATGGCGGTACCGGCGACGTGACTGTCGCCCCAAGCA
ACTTCGCTAACGGGGTCGCTGAATGGATCAGCTCTAACTCGCGTTCACAGGCTTACAAAGTA
ACCTGTAGCGTTCGTCAGAGCTCTGCGCAGAATCGCAAATACACCATCAAAGTCGAGGTGC
CTAAAGTGGCAACCCAGACTGTTGGTGGTGTAGAGCTTCCTGTAGCCGCATGGCGTTCGTAC
TTAAATATGGAACTAACCATTCCAATTTTCGCTACGAATTCCGACTGCGAGCTTATTGTTAA
GGCAATGCAAGGTCTCCTAAAAGATGGAAACCCGATTCCCTCAGCAATCGCAGCAAACTCC
GGCATCTACTAATAGACGCCGGGTTAATTAATTAAGGATCCGGCTGCTAACAAAGCCCGAA
AGGAAGCTGAGTTGGCTGCTGCCACCGCTGAGCAATAACTAGCATAACCCCTTGGGGCCTCT
AAACGGGTCTTGAGGGGTTTTTTGCTGAAAGGAGGAACTATATCCGGATATCCACAGGACG
GGTGTGGTCGCCATGATCGCGTAGTCGATAGTGGCTCCAAGTAGCGAAGCGAGCAGGACTG
GGCGGCGGCCAAAGCGGTCGGACAGTGCTCCGAGAACGGGTGCGCATAGAAATTGCATCAA
CGCATATAGCGCTAGCAGCACGCCATAGTGACTGGCGATGCTGTCGGAATGGACGATATCC
CGCAAGAGGCCCGGCAGTACCGGCATAACCAAGCCTATGCCTACAGCATCCAGGGTGACGG
TGCCGAGGATGACGATGAGCGCATTGTTAGATTTCATACACGGTGCCTGACTGCGTTAGCAA
TTTAACTGTGATAAACTACCGCATTAAAGCTTATCGATGATAAGCTGTCAAACATGAA

FIGURE 5

The nucleotide sequence (SEQ ID NO: 2) of the plasmid pDSP62 containing the F antigen peptide S10.5 inserted into the AB-loop of one copy of the single-chain dimer.

TTCTTAGAAAAACTCATCGAGCATCAAATGAAACTGCAATTTATTCATATCAGGATTATCAA
TACCATATTTTTGAAAAAGCCGTTTCTGTAATGAAGGAGAAAACTCACCGAGGCAGTTCCAT
AGGATGGCAAGATCCTGGTATCGGTCTGCGATTCCGACTCGTCCAACATCAATACAACCTAT
TAATTTCCCCTCGTCAAAAATAAGGTTATCAAGTGAGAAATCACCATGAGTGACGACTGAAT
CCGGTGAGAATGGCAAAAGCTTATGCATTTCTTTCCAGACTTGTTCAACAGGCCAGCCATTA
CGCTCGTCATCAAAATCACTCGCATCAACCAAACCGTTATTCATTCGTGATTGCGCCTGAGC
GAGACGAAATACGCGATCGCTGTTAAAAGGACAATTACAAACAGGAATCGAATGCAACCG
GCGCAGGAACACTGCCAGCGCATCAACAATATTTTCACCTGAATCAGGATATTCTTCTAATA
CCTGGAATGCTGTTTTCCCGGGGATCGCAGTGGTGAGTAACCATGCATCATCAGGAGTACGG
ATAAAATGCTTGATGGTCGGAAGAGGCATAAATTCCGTCAGCCAGTTTAGTCTGACCATCTC
ATCTGTAACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGCCCATTTA
TACCCATATAAATCAGCATCCATGTTGGAATTTAATCGCGGCCTCGAGCAAGACGTTTCCCG
TTGAATATGGCTCATAACACCCCTTGTATTACTGTTTATGTAAGCAGACAGTTTTATTGTTCA
TGACCAAAATCCCTTAACGTGAGTTTTCGTTCCACTGAGCGTCAGACCCCGTAGAAAAGATC
AAAGGATCTTCTTGAGATCCTTTTTTTCTGCGCGTAATCTGCTGCTTGCAAACAAAAAAACC
ACCGCTACCAGCGGTGGTTTGTTTGCCGGATCAAGAGCTACCAACTCTTTTTCCGAAGGTAA
CTGGCTTCAGCAGAGCGCAGATACCAAATACTGTCCTTCTAGTGTAGCCGTAGTTAGGCCAC
CACTTCAAGAACTCTGTAGCACCGCCTACATACCTCGCTCTGCTAATCCTGTTACCAGTGGC
TGCTGCCAGTGGCGATAAGTCGTGTCTTACCGGGTTGGACTCAAGACGATAGTTACCGGATA
AGGCGCAGCGGTCGGGCTGAACGGGGGGTTCGTGCACACAGCCCAGCTTGGAGCGAACGAC
CTACACCGAACTGAGATACCTACAGCGTGAGCTATGAGAAAGCGCCACGCTTCCCGAAGGG
AGAAAGGCGGACAGGTATCCGGTAAGCGGCAGGGTCGGAACAGGAGAGCGCACGAGGGAG
CTTCCAGGGGGAAACGCCTGGTATCTTTATAGTCCTGTCGGGTTTCGCCACCTCTGACTTGA
GCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGA
ACGACCGAGCGCAGCGAGTCAGTGAGCGAGGAAGCGGAAGAGCGCCTGATGCGGTATTTTC
TCCTTACGCATCTGTGCGGTATTTCACACCGCATATATGGTGCACTCTCAGTACAATCTGCTC
TGATGCCGCATAGTTAAGCCAGTATACACTCCGCTATCGCTACGTGACTGGGTCATGGCTGC
GCCCCGACACCCGCCAACACCCGCTGACGCGCCCTGACGGGCTTGTCTGCTCCCGGCATCCG

FIGURE 5 (CONT'D)

CTTACAGACAAGCTGTGACCGTCTCCGGGAGCTGCATGTGTCAGAGGTTTTCACCGTCATCA
CCGAAACGCGCGAGGCAGCTGCGGTAAAGCTCATCAGCGTGGTCGTGAAGCTTTTCAAAAT
TGTAAACGTTAATATTTTGTTAAAATTCGCGTTAAATTTTTGTTAAATCAGCTCATTTTTTAA
CCAATAGGCCGAAATCGGCAAAATCCCTTATAAATCAAAAGAATAGCCCGAGATAGGGTTG
AGTGTTGTTCCAGTTTGGAACAAGAGTCCACTATTAAAGAACGTGGACTCCAACGTCAAAG
GGCGAAAAACCGTCTATCAGGGCGATGGCCCACTACGTGAACCATCACCCAAATCAAGTTT
TTGGGGTCGAGGTGCCGTAAAGCACTAAATCGGAACCCTAAAGGGAGCCCCGATTTAGAG
CTTGACGGGGAAAGCCGGCGAACGTGGCGAGAAAGGAAGGGAAGAAAGCGAAAGGAGCG
GGCGCTAGGGCGCTGGCAAGTGTAGCGGTCACGCTGCGCGTAACCACCACACCCGCCGCGC
TTAATGCGCCGCTACAGGGCGCGTACTATGGTTGCTTTGACGTCGGCCGCCATGCCGGCGAT
AATGGCCTGCTTCTCGCCGAAACGTTTGGTGGCGGGACCAGTGACGAAGGCTTGAGCGAGG
GCGTGCAAGATTCCGAATACCGCAAGCGACAGGCCGATCATCGTCGCGCTCCAGCGAAAGC
GGTCCTCGCCGAAAATGACCCAGAGCGCTGCCGGCACCTGTCCTACGAGTTGCATGATAAA
GAAGACAGTCATAAGTGCGGCGACGATAGTCATGCCCCGCGCCCACCGGAAGGAGCTGACT
GGGTTGAAGGCTCTCAAGGGCATCGGCTCTCCCTTATGCGACTCCTGCATTAGGAAGCAGCC
CAGTAGTAGGTTGAGGCCGTTGAGCACCGCCGCCGCAAGGAATGGTGCATGCAAGGAGATG
GCGCCCAACAGTCCCCCGGCCACGGGGCCTGCCACCATACCCACGCCGAAACAAGCGCTCA
TGAGCCCGAAGTGGCGAGCCCGATCTTCCCCATCGGTGATGTCGGCGATATAGGCGCCAGC
AACCGCACCTGTGGCGCCGGTGATGCCGGCCACGATGCGTCCGGCGTAGAGGATCGAGATC
TCGATCCCGCGAAATTAATACGACTCACTATAGGGAGACCACAACGGTTTCCCTCTAGAAAT
AATTTTGTTTAACTTTAAGAAGGAGATATACCATGGCAAGCAATTTCACGCAATTTGTATTG
GTAGATAACGGGGGTACGGGGGATGTTACGGTAGCACCTTCAAATTTTGCAAATGGTGTAG
CAGAGTGGATATCAAGCAATAGCAGAAGCCAAGCATATAAGGTTACGTGCTCAGTAAGACA
ATCAAGCGCTCAAAACAGAAAGTATACGATAAAGGTAGAAGTTCCGAAGGTTGCTACGCAA
ACGGTAGGTGGTGTTGAATTGCCGGTTGCAGCTTGGAGAAGCTATCTCAACATGGAGTTGAC
GATACCTATATTTGCAACCAACAGTGATTGTGAATTGATAGTAAAAGCTATGCAGGGGTTGT
TGAAGGACGGTAATCCTATACCGAGCGCTATAGCTGCTAATAGTGGCCTCTACGGCAACTTT
ACTCAGTTCGTTCTCGTCGACAATGGCATGCCGATCACCAACGACCAGAAAAAACTGGGCG
ACGTGACTGTCGCCCCAAGCAACTTCGCTAACGGGGTCGCTGAATGGATCAGCTCTAACTCG
CGTTCACAGGCTTACAAAGTAACCTGTAGCGTTCGTCAGAGCTCTGCGCAGAATCGCAAATA
CACCATCAAAGTCGAGGTGCCTAAAGTGGCAACCCAGACTGTTGGTGGTGTAGAGCTTCCT
GTAGCCGCATGGCGTTCGTACTTAAATATGGAACTAACCATTCCAATTTTCGCTACGAATTC
CGACTGCGAGCTTATTGTTAAGGCAATGCAAGGTCTCCTAAAAGATGGAAACCCGATTCCCT
CAGCAATCGCAGCAAACTCCGGCATCTACTAATAGACGCCGGGTTAATTAATTAGGATCCG
GCTGCTAACAAAGCCCGAAAGGAAGCTGAGTTGGCTGCTGCCACCGCTGAGCAATAACTAG

FIGURE 5 (CONT'D)

CATAACCCCTTGGGGCCTCTAAACGGGTCTTGAGGGGTTTTTTGCTGAAAGGAGGAACTATA
TCCGGATATCCACAGGACGGGTGTGGTCGCCATGATCGCGTAGTCGATAGTGGCTCCAAGT
AGCGAAGCGAGCAGGACTGGGCGGCGGCCAAAGCGGTCGGACAGTGCTCCGAGAACGGGT
GCGCATAGAAATTGCATCAACGCATATAGCGCTAGCAGCACGCCATAGTGACTGGCGATGC
TGTCGGAATGGACGATATCCCGCAAGAGGCCCGGCAGTACCGGCATAACCAAGCCTATGCC
TACAGCATCCAGGGTGACGGTGCCGAGGATGACGATGAGCGCATTGTTAGATTTCATACAC
GGTGCCTGACTGCGTTAGCAATTTAACTGTGATAAACTACCGCATTAAAGCTTATCGATGAT
AAGCTGTCAAACATGAA

Figure 6. The p2P7K32 plasmid.
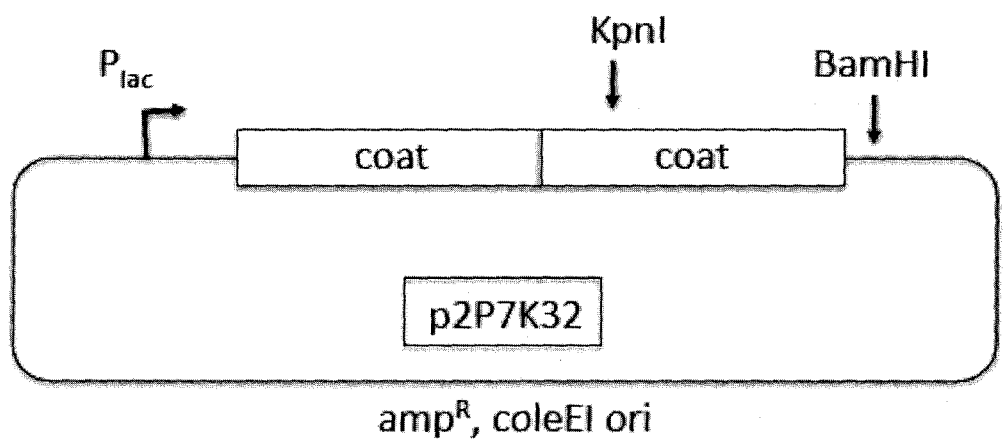

US 9,884,107 B2

IMMUNOGENIC RESPIRATORY SYNCYTIAL VIRUS GLYCOPROTEIN-CONTAINING VLPS AND RELATED COMPOSITIONS, CONSTRUCTS, AND THERAPEUTIC METHODS

RELATED APPLICATIONS

This application is a United States continuation patent application which is a continuation of U.S. national phase patent application Ser. No. 13/820,891 filed Apr. 4, 2013, which is based upon international patent application number PCT/US2011/051330 filed Sep. 13, 2011, which claims the benefit of priority of U.S. provisional application Ser. No. 61/382,704, of identical title, filed Sep. 14, 2010, the entire contents of which is incorporated by reference herein.

GOVERNMENT INTEREST

This invention was made with government support under Grant No. GM042901 awarded by the National Institutes of Health. The government has certain rights in the invention.

FIELD OF THE INVENTION

In one aspect, the invention provides immunogenic Respiratory Syncytial Virus (RSV) glycoprotein-containing viral-like particles (VLPs). In certain aspects, the invention provides immunogenic RSV G and F glycoprotein-containing VLPs. Related compositions (e.g. vaccines), nucleic acid constructs, and therapeutic methods are also provided.

In one aspect, the invention relates generally to virus-like particles and, more specifically, to a platform for peptide display based on VLPs of the RNA bacteriophage PP7.

In certain aspects, the VLPs are comprised of a coat polypeptide of the bacteriophages PP7 or MS2, wherein the coat protein is modified by insertion of peptide antigens derived from a RSV glycoprotein (e.g. a RSV G or F glycoprotein), the recombinant coat protein is expressed to produce a VLP, and wherein the RSV G or F glycoprotein peptide is displayed on the surface of the VLP.

Immunogenic VLPs and related compositions of the invention induce high titer antibody responses against a RSV glycoprotein (e.g. a RSV G or F glycoprotein) and may serve as a prophylactic or therapeutic vaccine for RSV infection.

BACKGROUND OF THE INVENTION

Respiratory Syncytial Virus (RSV) is a human pathogen that is the predominant cause of acute lower respiratory tract infection in children [reviewed by (27)]. In the United States, nearly all children are infected with RSV by the age of three. Symptoms range from severe pneumonia and bronchiolitis to milder infections. Because of its prevalence, RSV is a major cause of serious respiratory illness requiring hospitalization in children. Significant morbidity and mortality are also associated with RSV infection of the elderly.

The viral genome encodes two major structural glycoproteins that are exposed on the surface of RSV virions, G and F. G is believed to play a role in viral attachment to a cellular receptor. F promotes fusion of the viral and cell membranes, allowing entry of the viral genome into the target cell. Antibodies against either G or F can neutralize RSV infectivity (18). The G protein is highly genetically diverse amongst RSV strains, thus anti-G neutralizing antibodies are only neutralizing against viruses of one of the two antigenic groups of RSV (either A or B). In contrast, F is highly conserved and anti-F neutralizing antibodies can protect animal models from infection by both group-A and group-B viruses (26, 31).

There is no current vaccine for RSV infection. (In the 1960s a formalin-inactivated RSV vaccine candidate actually increased disease severity in vaccinated children.) Moreover, there are no useful therapeutics for treating RSV infection. However, Palivizumab, also known by its trade name Synagis, a monoclonal antibody that targets a neutralizing epitope in the F glycoprotein, has been used prophylactically to prevent RSV infection. Although Synagis is effective, it is very expensive and only is cost-effective for use in infants that are at extremely high risk for developing severe RSV infection. Because of its expense, it is only used in developed countries.

Virus-like Particle (VLP) Based Vaccines.

Virus-like particles (VLPs) make excellent vaccines. They are non-infectious, often easier to produce than actual viruses, and, because the regularity of their capsid structure presents viral epitopes as dense, highly repetitive arrays that strongly stimulate B cells, they are highly immunogenic. VLPs are comprised of one or more proteins arranged geometrically into dense, repetitive arrays. These structures are largely unique to microbial antigens, and the mammalian immune system has apparently evolved to respond vigorously to this arrangement of antigens. B cells specifically recognize and respond strongly to the ordered array of densely spaced repetitive elements characteristic of virus surfaces (1, 16). Highly repetitive antigens provoke oligomerization of the membrane-associated immunoglobulin (Ig) molecules that constitute the B cell receptor (BCR) (2). There is evidence that the Ig crosslinking mediated by multivalent antigens leads to the formation of highly stable BCR-signaling microdomains that are associated with increased signaling to the B cell (34). This signaling stimulates B cell proliferation, migration, and upregulation of both major histocompatibility complex (MHC) class II and the co-stimulatory molecules that permit subsequent interactions with T helper cells that are required to trigger IgG secretion, affinity maturation, and the generation of long-lived memory B cells (8). Consequently, multivalent antigens such as VLPs can activate B cells at much lower concentrations than monomeric antigens (3, 13, 14, 25). Hence, VLPs are innately immunogenic: they induce high titer and long lasting antibody responses at low doses, often without requiring adjuvants (19, 36).

VLPs as Flexible Platforms for Vaccine Development.

VLPs can be used as the basis for vaccines targeting the virus from which they were derived (the Hepatitis B virus vaccine and HPV vaccine are two clinically approved VLP vaccines, other VLP vaccines are in clinical trials). However, they also can be used as platforms to display practically any epitope in a highly immunogenic, multivalent format. Heterologous antigens displayed at high density on the surface of VLPs exhibit the same high immunogenicity as unmodified VLPs. VLPs derived from a variety of different viruses have been exploited in this manner to induce antibody responses against heterologous targets that are poorly immunogenic in their native contexts. Although the VLP platform strategy has typically been applied to target antigens derived from pathogens, VLP-display can effectively induce antibody responses against practically any antigen. One example is the vaccine for nicotine addiction (designed to assist smokers who are trying to quit) developed by a biotechnology company, Cytos Biotechnology. This vaccine consists of nicotine, conjugated at high copy number to the surface of VLPs derived from a bacteriophage. In phase II clinical trials, VLPs displaying nicotine were well-tolerated and induced strong nicotine-specific IgG responses in 100% of immunized subjects (12). Even self-antigens, which are normally subject to the mechanisms of B cell tolerance, are immunogenic when displayed at high density on the surface of VLPs. Vaccines have been developed against self-molecules involved in several different diseases, including amyloid-beta (Alzheimers (11, 21)), TNF-α (arthritis (9)), CCR5 (HIV infection (7, 10)), gastrin (cancer, unpublished data), IgE (allergy, unpublished data), and others. VLP-based vaccines developed by pharmaceutical companies targeting amyloid-beta and angiotensin II (hypertension) are currently being evaluated in clinical trials; positive results from the trial of vaccine targeting angiotensin II (as a vaccine for hypertension) were reported in the spring of 2008 (35).

Objects of the Invention

It is an object of the invention to provide a virus-like particle (VLP) virus-like particle comprising a bacteriophage single chain coat polypeptide dimer, preferably based upon a MS2 or PP7 bacteriophage and a RSV peptide (preferably an epitope within RSV glycoprotein G or F, wherein the RSV peptide is displayed on the virus-like particle and said VLP encapsidates bacteriophage mRNA, such that the composition is immunotherapeutic and prophylactic for RSV infections and/or RSV-induced disorders and/or secondary disease states and conditions.

It is another object of the invention to provide nucleic acid constructs which express a VLP comprising a bacteriophage single chain coat polypeptide dimer, preferably based upon a MS2 or PP7 bacteriophage and an epitope within RSV glycoprotein G or F, wherein the RSV peptide is displayed on the viral-like particle and wherein said VLP encapsidates bacteriophage mRNA.

It is another object of the invention to provide a method of instilling immunogenicity or prophylaxis to a RSV infection and/or a RSV related disorder in a patient at risk for such an infection or disorder.

Providing an immunogenic response to a RSV peptide in a subject represents an additional object of the invention.

Providing a vaccine against RSV infection and/or an RSV-related disorder with low toxicity and minimal side effects represents a further object of the present invention.

SUMMARY OF THE INVENTION

The need exists for a cost-effective, widely-applicable RSV vaccine that can be used in the inoculation and treatment of a broad-range of patients, including infants who are at a high risk for developing severe RSV infection.

Previously we described the use of virus-like particles (VLPs) of two RNA bacteriophages, MS2 and PP7, for peptide display (6, 30). MS2 and PP7 coat protein single-chain dimers are highly tolerant of peptide insertions and produce correctly assembled VLPs displaying the peptide insertion on the surface of VLP in a highly dense, repetitive array. These VLPs are highly immunogenic and confer this high immunogenicity to heterologous peptides displayed on their surfaces. Here we describe VLPs displaying peptide antigens derived from Respiratory Syncytial Virus (RSV) glycoproteins such as RSV glycoproteins G and F. Such recombinant VLPs serve as an immunogenic material and prophylactic vaccine to prevent infection by RSV.

The invention provides immunotherapeutic and prophylactic bacteriophage viral-like particle (VLPs) which are useful in the treatment and prevention of RSV and related disorders. Related compositions (e.g. vaccines), nucleic acid constructs, and therapeutic methods are also provided. VLPs and related compositions of the invention induce high titer antibody responses against RSV. VLPs, VLP-containing compositions, and therapeutic methods of the invention induce an immunogenic response against RSV neutralizing epitopes.

Because antibodies that are specific for highly conserved epitopes within RSV glycoproteins G and F are able to neutralize infection by a broad range of RSV types, RSV glycoproteins G and F-targeting VLPs and related compositions (e.g. vaccines) of the invention provide a more comprehensive protection against infection by multiple RSV types.

In one aspect, the invention provides a VLP comprising a bacteriophage single chain coat polypeptide dimer and a RSV peptide (e.g. a RSV G or F peptide, preferably F peptide of about 3 to about 30, more preferably about 5 to about 20, about 5 to about 15, about 5 to about 10 amino acid units in length), wherein the RSV peptide is displayed on the VLP, and wherein the VLP produces an immunogenic response in a subject and/or is immuno-prophylactic for RSV-induced disorders.

Certain aspects of the invention reflect that the single-chain dimer of MS2 and PP7 coat protein can tolerate the insertion of a wide variety of peptides, including peptides derived from different strains of RSV, can self-assemble into VLPs, and is highly immunogenic.

In another aspect, the invention provides a composition comprising a VLP comprising a bacteriophage single chain coat polypeptide dimer and a RSV peptide (e.g. a RSV G or F peptide, preferably F peptide of 3 to 30, more preferably 5 to 20 amino acid units in length), wherein the RSV peptide is displayed on the VLP, and wherein the composition is immunotherapeutic and prophylactic for RSV-induced disorders.

In certain aspects, the invention provides a VLP, or a composition comprising a VLP, wherein the VLP is made by transforming a prokaryote with a nucleic acid construct comprising:
(a) a bacterial or bacteriophage promoter;
(b) a coding sequence of a bacteriophage single chain coat polypeptide dimer which is operably associated with the promoter and which is modified to contain a nucleotide sequence encoding a RSV peptide (e.g. RSV G or F peptide, preferably F peptide of 3 to 30, more preferably 5 to 20 amino acid units in length);
(c) an antibiotic repressor which is operably associated with the promoter; and
(d) a replication origin for replication in a prokaryotic cell, wherein the composition is immunotherapeutic and prophylactic for RSV-induced disorders.

In certain aspects, VLPs and VLP-containing compositions (e.g. vaccines) of the invention are comprised of VLPs comprising RSV peptides from different RSV types. In other aspects, VLPs and VLP-containing compositions of the invention comprise hybrid VLPs that display multiple RSV sequences.

In certain aspects, the invention provides a VLP, or a composition comprising a VLP, wherein the VLP is made by transforming a prokaryote with a nucleic acid construct comprising either:
(1) (a) a bacterial or bacteriophage promoter which is operably associated with a coding sequence of a bacteriophage (preferably PP7) single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within, the sequence which defines the coat polypeptide dimer AB loop, and (ii) contain a nucleotide sequence encoding a RSV peptide (e.g. a RSV G or F peptide, preferably a F peptide of 3 to 30, more preferably 5 to 20 amino acid units in length);
(b) a second restriction site positioned 3' to the coat polypeptide dimer coding sequence;
(c) an antibiotic repressor which is operably associated with the promoter; and
(d) a replication origin for replication in a prokaryotic cell; or
(2) (a) a bacterial or bacteriophage promoter which is operably associated with a coding sequence of a bacteriophage (preferably PP7), single chain coat polypeptide dimer, wherein the coat polypeptide dimer coding sequence is modified to: (i) define a first restriction site which is located in the downstream portion of the coat polypeptide dimer coding sequence and which is either positioned 5' to, or located within, the sequence which defines the coat polypeptide dimer AB loop, and (ii) contain a nucleotide sequence encoding a RSV peptide (e.g. a RSV G or F peptide, preferably a F peptide of 3 to 30, more preferably 5 to 20 amino acid units in length);
(b) a second restriction site positioned 3' to the coat polypeptide dimer coding sequence;
(c) a PCR primer positioned 3' to the second restriction site;
(d) an antibiotic repressor which is operably associated with the promoter; and
(e) a replication origin for replication in a prokaryotic cell; or
(3) (a) a bacterial or bacteriophage promoter which is operably associated with a coding sequence of a bacteriophage (preferably MS2) single chain coat polypeptide dimer, wherein the coat polypeptide dimer coding sequence is modified to (i) define a codon sequence positioned 5' to that portion of the sequence which defines the coat polypeptide dimer AB loop, and (ii) contain a nucleotide sequence encoding a RSV peptide (e.g. a RSV G or F peptide, preferably a F peptide of 3 to 30, more preferably 5 to 20 amino acid units in length);
(b) a restriction site positioned 3' to the coat polypeptide dimer coding sequence;
(c) a PCR primer positioned 3' to the second restriction site;
(d) a repressor to resistance to a first antibiotic, wherein the repressor is operably associated with the promoter;
(e) a helper phage gene modified to contain a gene conferring resistance to a second antibiotic, and
(f) a replication origin for replication in a prokaryotic cell.

In certain aspects, the invention provides a method of generating an immunogenic response to a RSV peptide, the method comprising administering to a subject an effective amount of a RSV peptide-containing VLP as otherwise described herein, optionally in combination with a pharmaceutically acceptable carrier, additive or excipient. In certain aspects, the invention provides a method of inoculating a subject at risk of developing a RSV infection or a RSV-related disorder, the method comprising administering to the subject one or more doses of a composition comprising a RSV peptide-containing (e.g. RSV G or F peptide-containing, preferably F peptide-containing of 3 to 30, more preferably 5 to 20 amino acid units in length) VLP as described herein. In other aspects, the invention provides a method of treating a subject who is at risk of developing a RSV-related disorder and who has undergone RSV seroconversion, the method comprising administering to the subject one or more doses of a composition comprising a RSV peptide containing VLP as described herein. In still other aspects, the invention provides a method of treating a subject who has developed a RSV-related disorder, the method comprising administering to the subject one or more doses of a composition comprising a RSV-containing VLP as described herein.

Previously, we described the use of VLPs of the RNA bacteriophage MS2 for peptide display. By genetically fusing two copies of the MS2 coat protein, we created a single-chain dimer with increased thermodynamic stability and vastly improved tolerance of insertions in its AB-loop (30). The MS2 coat protein dimer was widely tolerant of genetic insertion of defined peptide sequences as well as random peptide insertions. Recombinant MS2 VLPs elicited high titer IgG antibodies against the inserted sequences. Moreover, MS2 coat protein single-chain dimers produced correctly assembled VLPs that specifically encapsidated the mRNA encoding their synthesis, raising the possibility that they could be used in affinity selections protocols analogous to filamentous phage display.

Since MS2 is only one member of a large family of bacteriophages whose individual members share similar molecular biology, we suspected that, following similar design principles, other phage VLPs could be adapted to this same purpose. For example, we include hereinafter our previous description in U.S. Provisional Patent Application Ser. Nos. 61/302,836, filed Feb. 9, 2010, 61/334,826, filed May 14, 2010 and PCT application no. PCT/US2011/24030, filed 8 Feb. 2011 (the complete contents of which are hereby incorporated by reference) of the engineering of VLPs of PP7, a bacteriophage of Pseudomonas aeruginosa, for the purposes of peptide display.

PP7 VLPs offer several potential advantages and improvements over the MS2 VLP. First, the particles are dramatically more stable thermodynamically, because of the presence of stabilizing inter-subunit disulfide bonds. For many practical applications, including vaccines, increased stability is a desirable trait. Second, PP7 VLPs are not cross-reactive immunologically with those of MS2. This could be important in applications where serial administration of VLPs may be necessary. Third, we anticipated that the correct folding and assembly of the PP7 VLP might be more resistant to the destabilizing effects of peptide insertion, or that it might at least show tolerance of some peptides not tolerated in MS2 VLPs.

The single-chain dimer of PP7 coat protein can tolerate the insertion of a wide variety of peptides, is highly immunogenic, and packages the RNA that directs its synthesis. Moreover, we have shown in U.S. Provisional Patent Application Ser. No. U.S. Provisional Patent Application Ser. Nos. 61/302,836, filed Feb. 9, 2010, 61/334,826, filed May 14, 2010 and PCT application no. PCT/US2011/24030, filed 8 Feb. 2011 (the complete contents of which are hereby incorporated by reference) that an in vivo challenge model that a PP7 VLP displaying a broadly cross-type neutralizing epitope from the HPV minor capsid protein L2 induces antibodies that protect against homologous and heterologous HPV infection.

Thus, we describe the use of recombinant VLPs derived RNA bacteriophages to induce high titer antibody responses against RSV G or F peptide that protect against multiple diverse RSV types.

These and other aspects of the invention are described further in the Detailed Description of the Invention.

BRIEF DESCRIPTION OF THE FIGURES

FIG. 1. A. The nucleotide and amino acid sequence of target regions in the RSV F and G glycoproteins. B. The N-terminal sequence the downstream copy of coat protein encoded by pDSP62 (MS2) or p2P7K32 (PP7). C. A list of the forward primers used to clone the listed sequences into MS2 coat (shown 5' to 3'). The SalI restriction site is shown in italics and the peptide insertion is shown in bold text. A similar strategy was used to clone these sequences into the PP7 expression vector. Sequences were inserted into PP7 at amino acid 11, resulting in a duplication of this residue D. A list of the MS2 primers used to construct G pepetide insertions.

FIG. 3 depicts the pDSP1 plasmid and a technique for inserting a nucleic acid sequence encoding a heterologous peptide into that plasmid.

FIG. 4 (N12-150) contains the nucleic acid sequence for the pDSP1 plasmid (SEQ ID NO: 1).

FIG. 5 shows the nucleotide sequence the plasmid pDSP62 containing the F antigen peptide S10.5 inserted into the AB-loop of one copy of the single-chain dimer (SEQ ID NO: 2).

FIG. 6 depicts the p2P7K32 plasmid.

DETAILED DESCRIPTION OF THE INVENTION

Figure 2:
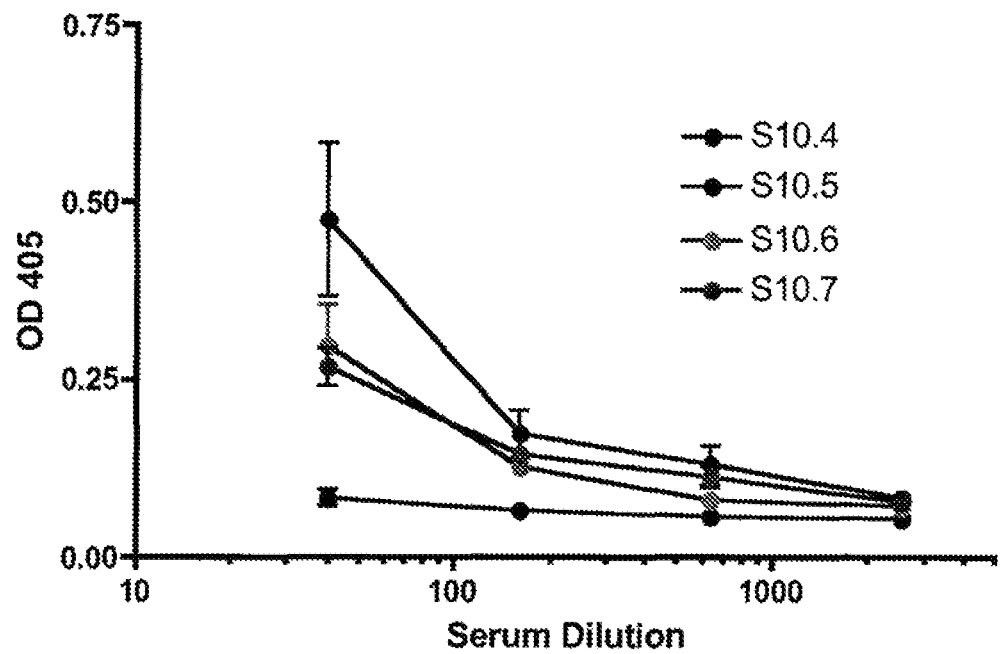
FIG. 2. Anti-RSV antibody responses induced by recombinant MS2 VLPs. Groups of three mice were immunized three times (at weeks 0, 2, and 5) with 10 µg of VLPs plus incomplete Freund's adjuvant. Two weeks after the final immunization mice were bled and sera from individual mice were tested for reactivity with a peptide representing the "Synagis" epitope (Leu-Thr-Asn-Ser-Glu-Leu-Leu-Ser-Leu-Ile-Asn-Asp-Met-Pro-Ile-Thr-Asn-Asp-Gln-Lys-Lys-Leu-Met-Ser-Asn-Asn-Val) (panel A), or pooled sera from each group were tested for reactivity with recombinant F antigen (purchased from Sino Biological Inc.; panel B), or with UV-inactivated RSV virions (purchased from Fitzgerald Industries; panels C and D) by ELISA. The results above show the IgG antibody titer for individual mice (panel A) or ELISA values (represented as optical density at 405 nm; OD405, panels B, C, and D) for pooled sera from each group of three mice at various serum dilutions. Error bars indicate the standard error of the mean (SEM).
Figure 2:
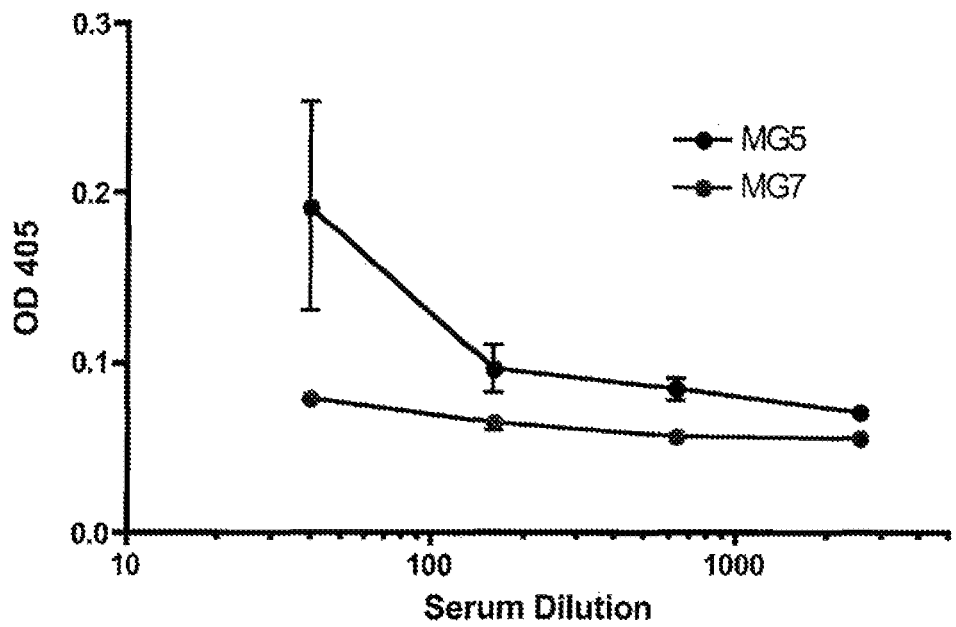

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984,"Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Furthermore, the following terms shall have the definitions set out below.

The term "patient" or "subject" is used throughout the specification within context to describe an animal, generally a mammal and preferably a human, to whom treatment, including prophylactic treatment (prophylaxis), with the immunogenic compositions and/or vaccines according to the present invention is provided to inoculate and/or generate an immunogenic response. For treatment of those infections, conditions or disease states which are specific for a specific animal such as a human patient, the term patient refers to that specific animal. In most instances, the patient or subject of the present invention is a human patient of either or both genders.

The term "effective" is used herein, unless otherwise indicated, to describe a number of VLP's or an amount of a VLP-containing composition which, in context, is used to produce or effect an intended result, whether that result relates to the prophylaxis and/or therapy of a RSV infection or RSV-induced or RSV-related disorder (or secondary disease state or condition) or as otherwise described herein. The term effective subsumes all other effective amount or effective concentration terms (including the term "therapeutically effective") which are otherwise described or used in the present application.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

The amino acid residues described herein are preferred to be in the "L" isomeric form. However, residues in the "D" isomeric form can be substituted for any L-amino acid residue, as long as the desired functional is retained by the polypeptide. $NH_2$ refers to the free amino group present at the amino terminus of a polypeptide. COOH refers to the free carboxy group present at the carboxy terminus of a polypeptide.

The term "single-chain dimer" refers to a normally dimeric protein whose two subunits have been genetically (chemically, through covalent bonds) fused into a single polypeptide chain. Specifically, in the present invention single-chain dimer versions of PP7 coat proteins were constructed. Each of these proteins is naturally a dimer of identical polypeptide chains. In the PP7 coat protein dimers the N-terminus of one subunit lies in close physical proximity to the C-terminus of the companion subunit. Single-chain coat protein dimers were produced using recombinant DNA methods by duplicating the DNA coding sequence of the coat proteins and then fusing them to one another in tail to head fashion. The result is a single polypeptide chain in which the coat protein amino acid appears twice, with the C-terminus of the upstream copy covalently fused to the N-terminus of the downstream copy. Normally (wild-type) the two subunits are associated only through noncovalent interactions between the two chains. In the single-chain dimer these noncovalent interactions are maintained, but the two subunits have additionally been covalently tethered to one another. This greatly stabilizes the folded structure of the protein and confers to it its high tolerance of peptide insertions as described above.

VLPs according to the present invention (especially those based upon PP7 and MS2 coat polypeptide dimers), because of their use of single-chain dimers as described above, exhibit a number of advantages over traditional approaches for providing vaccines, including vaccines based upon prior art viral particles. For examples, VLPs according to the present invention exhibit exceptional stability, ease of manufacture, higher yields during manufacturing and they are regular in appearance with greater consistency, resulting in a more reliable immunogenic response with lower toxicity and fewer side effects.

This application makes reference to coat protein's "AB-loop". The RNA phage coat proteins possess a conserved tertiary structure. The PP7 coat proteins, for example, possess a structure wherein each of the polypeptide chains is folded into of a number of β-strands. The β-strands A and B form a hairpin with a three-amino acid loop connecting the two strands at the top of the hairpin, where it is exposed on the surface of the VLP. As evidenced in the present application, peptides inserted into the AB-loop are exposed on the surface of the VLP and are strongly immunogenic.

The term "valency" is used to describe the density of a RSV peptide display on VLPs according to the present invention. Valency in the present invention may range from low valency to high valency, about less than 1 to more than about 180, preferably about 90 to 180. Immunogenic compositions according to the present invention comprise VLPs which are preferably high valency and comprise VLPs which display at least 50-60 up to about 180 or more RSV peptides.

The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

A "heterologous" region of a recombinant cell is an identifiable segment of nucleic acid within a larger nucleic acid molecule that is not found in association with the larger molecule in nature.

An "origin of replication", used within context, normally refers to those DNA sequences that participate in DNA synthesis by specifying a DNA replication initiation region. In the presence of needed factors (DNA polymerases, and the like) an origin of replication causes or facilitates DNA associated with it to be replicated. By way of a non-limiting example, the ColE1 replication origin endows many commonly used plasmid cloning vectors with the capacity to replicate independently of the bacterial chromosome. Another example is the p15A replication origin. The presence on a plasmid of an additional origin of replication from phage M13 confers the additional ability to replicate using that origin when E. coli cells are infected with a so-called helper phage (e.g. M13CM1) which provides necessary protein factors. M13 replicates intracellularly as double-stranded circular DNA, but also produces a single-stranded circular form, which it packages within the phage particle. These particles provide a convenient source of single-stranded circular DNA for plasmids.

A "promoter sequence" is a DNA regulatory region capable of binding RNA polymerase in a cell and initiating transcription of a downstream (3' direction) coding sequence. For purposes of defining the present invention, the promoter sequence includes the minimum number of bases or elements necessary to initiate transcription at levels detectable above background. Within the promoter will be found DNA sequences responsible for the binding of RNA polymerase and any of the associated factors necessary for transcription initiation. In bacteria promoters normally consist of −35 and −10 consensus sequences and a more or less specific transcription initiation site. Eukaryotic promoters will often, but not always, contain "TATA" boxes and "CAT" boxes. Bacterial expression vectors (usually plasmids or phages) typically utilize promoters derived from natural sources, including those derived from the E. coli Lactose, Arabinose, Tryptophan, and ProB operons, as well as others from bacteriophage sources. Examples include promoters from bacteriophages lambda, T7, T3 and SP6.

In bacteria, transcription normally terminates at specific transcription termination sequences, which typically are categorized as rho-dependent and rho-independent (or intrinsic) terminators, depending on whether they require the action of the bacterial rho-factor for their activity. These terminators specify the sites at which RNA polymerase is caused to stop its transcription activity, and thus they largely define the 3'-ends of the RNAs, although sometimes subsequent action of ribonucleases further trims the RNA.

An "antibiotic resistance gene" refers to a gene that encodes a protein that renders a bacterium resistant to a given antibiotic. For example, the kanamycin resistance gene directs the synthesis of a phosphotransferase that modifies and inactivates the drug. The presence on plasmids of a kanamycin resistance gene provides a mechanism to select for the presence of the plasmid within transformed bacteria. Similarly, the chloramphenicol resistance gene allows bacteria to grow in the presence of the drug by producing an acetyltransferase enzyme that inactivates the antibiotic through acetylation.

The term "PCR" refers to the polymerase chain reaction, a technique used for the amplification of specific DNA sequences in vitro. The term "PCR primer" refers to DNA sequences (usually synthetic oligonucleotides) able to anneal to a target DNA, thus allowing a DNA polymerase (e.g. Taq DNA polymerase) to initiate DNA synthesis. Pairs of PCR primers are used in the polymerase chain reaction to initiate DNA synthesis on each of the two strands of a DNA and to thus amplify the DNA segment between two primers. Representative PCR primers which used in the present invention are those which are presented in FIG. 1 hereof. Additional PCR primers may be obtained for the various RSV peptides which are presented herein.

Examples of primers used for PCR are given in FIG. 1 as described above and the following.
E3.2: 5' CGG GCT TTG TTA GCA GCC GG 3'—(SEQ ID No. 3) may serve as the 3' (reverse)-primer in PCR reactions to amplify coat protein.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence. Transcriptional control sequences are DNA regulatory sequences, such as promoters, enhancers, polyadenylation signals, terminators, and the like, that provide for the expression of a coding sequence in a host cell, Translational control sequences determine the efficiency of translation of a messenger RNA, usually by controlling the efficiency of ribosome binding and translation initiation. For example, as discussed elsewhere in this application, the coat proteins of the RNA phages are well-known translational repressors of the phage replicase. As coat protein accumulates to a sufficiently high concentration in the infected cell, it binds to an RNA hairpin that contains the translation initiation region (Shine-Dalgarno and initiator AUG) of the phage's replicase gene. This prevents ribosome binding and shuts off replicase synthesis at a time in the viral life cycle where the transition from replication to virus assembly occurs.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

It should be appreciated that also within the scope of the present invention are nucleic acid sequences encoding the polypeptide(s) of the present invention, which code for a polypeptide having the same amino acid sequence as the sequences disclosed herein, but which are degenerate to the nucleic acids disclosed herein. By "degenerate to" is meant that a different three-letter codon is used to specify a particular amino acid.

As used herein, "epitope" refers to an antigenic determinant of a polypeptide, in this case a RSV peptide. An epitope could comprise 3 amino acids in a spatial conformation which is unique to the epitope. Generally an epitope consists of at least 5 such amino acids, and more usually, consists of at least about 8-10 up to about 20 or more such amino acids. Methods of determining the spatial conformation of amino acids are known in the art, and include, for example, x-ray crystallography and 2-dimensional nuclear magnetic resonance.

As used herein, a "mimotope" is a peptide that mimics an authentic antigenic epitope, which epitope may include both peptide and carbohydrate epitopes.

As used herein, the term "coat protein(s)" refers to the protein(s) of a bacteriophage or a RNA-phage capable of being incorporated within the capsid assembly of the bacteriophage or the RNA-phage.

As used herein, a "coat polypeptide" as defined herein is a polypeptide fragment of the coat protein that possesses coat protein function and additionally encompasses the full length coat protein as well or single-chain variants thereof.

As used herein, the term "immune response" refers to a humoral immune response and/or cellular immune response leading to the activation or proliferation of B- and/or T-lymphocytes and/or antigen presenting cells. In some instances, however, the immune responses may be of low intensity and become detectable only when using at least one substance in accordance with the invention. "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

As used herein, the term "vaccine" refers to a formulation which contains the composition of the present invention and which is in a form that is capable of being administered to an animal and provides a measure of protection (protective effect) against a disease state or condition for which the vaccine is administered. The term "prevention" is used in context synonymously with the term "reducing the likelihood of" or "inhibiting" wherein the measure of prevention (of a disease state or condition) is one of degree of effect. Vaccines according to the present invention instill immunogenicity against a RSV peptide and may also instill immunity in a patient or subject against a disease state or condition (RSV or a related condition or disease state).

As used herein, the term "virus-like particle of a bacteriophage" refers to a virus-like particle (VLP) resembling the structure of a bacteriophage, being non replicative and noninfectious, and lacking at least the gene or genes encoding for the replication machinery of the bacteriophage, and typically also lacking the gene or genes encoding the protein or proteins responsible for viral attachment to or entry into the host. This definition should, however, also be seen to encompass virus-like particles of bacteriophages, in which the aforementioned gene or genes are still present but inactive, and, therefore, also leading to non-replicative and noninfectious virus-like particles of a bacteriophage.

VLP of RNA bacteriophage coat protein: The capsid structure formed from the self-assembly of one or more subunits of RNA bacteriophage coat protein and optionally containing host RNA is referred to as a "VLP of RNA bacteriophage coat protein". In a particular embodiment, the capsid structure is formed from the self assembly of 90-180 subunits.

A nucleic acid molecule is "operatively linked" to, or "operably associated with", an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

RSV-Induced Disorders, Immunogenicity, and Prophylactic Efficacy

Respiratory Syncytial Virus (RSV) is a human pathogen that is the predominant cause of acute lower respiratory tract infection in children [reviewed by (27)]. In the United States, nearly all children are infected with RSV by the age of three. Symptoms range from severe pneumonia and bronchiolitis to milder infections. Because of its prevalence, RSV is a major cause of serious respiratory illness requiring hospitalization in children. There are more than 26 strains within the two types/subgroups A and B of RSV. Unless otherwise indicated, the term RSV refers to the various strains of the virus. Significant morbidity and mortality are also associated with RSV infection of the elderly. The term "RSV-induced disorder" refers to a disease state, condition or symptomology which occurs in a patient secondary to, or as a consequence of RSV infection, including bronchiolitis and/or viral pneumonia and other symptomology associated with viral respiratory tract infection (wheezing, cough, high temperature, etc.).

RSV Glycoproteins, Peptides, and Peptide Sequences

"RSV" as used herein includes RSV Types A and B. "RSV glycoprotein peptide sequences" include RSV F and G glycoprotein peptide sequences, as well as all other RSV glycoprotein peptide sequences, e.g. as identified in (17).

Preferred RSV glycoprotein peptide sequences include epitopic peptide sequences comprising from 3 to 30, preferably 5 to 20 amino acid RSV F or G glycoprotein sequences, preferably from 5 to about 8-10 amino acids of RSV F or G glycoprotein sequences, preferably F glycoprotein sequences. Exemplary RSV epitopic peptide sequences which are preferably contained in VLP particles according to the present invention include, for example, contiguous peptide sequences of the F Antigen amino acid sequence presented hereinbelow ranging from 3 to 30, 5 to 20, 5 to 15, 5 to 12, 8 to 12, preferably 8-10 amino acid units.

```
F Antigen amino acid sequence (SEQ ID NO: 4):
  1 melpilkana ittilaavtf cfassqnite efyqstcsav skgylsalrt gwytsvitie 61 lsnikenkcn gtdakvklmk qeldkyknav telqllmqst paannrarre lprfmnytln 121 ntkktnvtls kkrkrrflgf llgvgsaias giavskvlhl egevnkiksa llstnkavvs 181 lsngvsvlts kvldlknyid kqllpivnkr scrisnietv iefqhknnrl leitrefsvn 241 agvttpvsty mltnsellsl indmpitndq kklmsnnvqi vrqqsysims iikeevlayv 301 vqlplygvid tpcwklhtsp lcttntkegs nicltrtdrg wycdnagsvs ffpqaetckv 361 qsnrvfcdtm nsltlpsevn lcnvdifnpk ydckimtskt dvsssvitsl gaivscygkt 421 kctasnknrg iiktfsngcd yvsnkgvdtv svgntlyyvn kqegkslyvk gepiinfydp 481 lvfpsdefda sisqvnekin qslafirksd ellhnvnagk sttnimitti ieeiivills 541 liavglllyc karstpvtls kdqlsginni afsn
```

Epitopic peptides from the F antigen of RSV are preferred for use in the present invention. Particularly preferred epitopic amino acid sequences may be readily obtained from antigenic site II, antigenic site IV or antigenic site I of the F antigen of RSV.

Contiguous peptide sequences (e.g., about 5-20, 5-15, 5-10, 8-10 contiguous amino acids) from the following sites of the F antigen, are particularly preferred:

1. The so-called antigenic site II (amino acids 252-278) (e.g., 3-28, 5-20, 5-15, 5-10, 6-10, 7-10, 8-10 contiguous amino acids of amino acids 252-278 of the antigenic site II):

```
                                          (SEQ ID NO: 5)
              LTNSELLSL INDMPITNDQ KKLMSNNV
```

2. Antigenic site IV (encompassing amino acids 429-437) (e.g. 3-20, 4-20, 5-20, 5-15, 5-10, 6-10, 7-10, 8-10 contiguous amino acids of amino acids 429-437 of the antigenic site IV):

```
                                          (SEQ ID NO: 6)
              KCTASNKNRGIIKTFSNGCD
```

3. Antigenic site I (encompassing amino acid 389) (e.g. 3-20, 4-20, 5-20, 5-15, 5-10, 6-10, 7-10, 8-10 contiguous amino acids of antigenic site I):

```
                                            (SEQ ID NO: 7)
LCNVDIFNPKYDCKIMTSKT
```

Other preferred epitopic peptide sequences can be readily provided from the list of sequences presented above and include the following:

Any 5-20 contiguous amino acids from antigenic site II (amino acids 252-278), presented above;
Any 5-15 contiguous amino acids from antigenic site II,
Any 5-12 contiguous amino acids from antigenic site II,
Any 5-10 contiguous amino acids from antigenic site II,
Any 6-11 contiguous amino acids from antigenic site II,
Any 6-10 contiguous amino acids from antigenic site II,
Any 7-10 contiguous amino acids from antigenic site II,
Any 8-10 contiguous amino acids from antigenic site II,
Any 6 contiguous amino acids from antigenic site II,
Any 7 contiguous amino acids from antigenic site II,
Any 8 contiguous amino acids from antigenic site II,
Any 9 contiguous amino acids from antigenic site II,
Any 10 contiguous amino acids from antigenic site II,
Any 11 contiguous amino acids from antigenic site II,
Any 12 contiguous amino acids from antigenic site II.
Any 5-20 contiguous amino acids from antigenic site IV (which encompasses amino acids 429-437), presented above;
Amino acids 429-437 of antigenic site IV;
Any 5 contiguous amino acids of amino acids 429-437 of antigenic site IV;
Any 6 contiguous amino acids of amino acids 429-437 of antigenic site IV;
Any 7 contiguous amino acids of amino acids 429-437 of antigenic site IV;
Either of the 8 contiguous amino acids of amino acids 429-437 of antigenic site IV;
Any 5-15 contiguous amino acids from antigenic site IV,
Any 5-12 contiguous amino acids from antigenic site IV,
Any 5-10 contiguous amino acids from antigenic site IV,
Any 6-11 contiguous amino acids from antigenic site IV,
Any 6-10 contiguous amino acids from antigenic site IV,
Any 7-10 contiguous amino acids from antigenic site IV,
Any 8-10 contiguous amino acids from antigenic site IV,
Any 6 contiguous amino acids from antigenic site IV,
Any 7 contiguous amino acids from antigenic site IV,
Any 8 contiguous amino acids from antigenic site IV,
Any 9 contiguous amino acids from antigenic site IV,
Any 10 contiguous amino acids from antigenic site IV,
Any 11 contiguous amino acids from antigenic site IV,
Any 12 contiguous amino acids from antigenic site IV.
Any 5-20 contiguous amino acids from antigenic site I, presented above;
Any 5-15 contiguous amino acids from antigenic site I,
Any 5-12 contiguous amino acids from antigenic site I,
Any 5-10 contiguous amino acids from antigenic site I,
Any 6-11 contiguous amino acids from antigenic site I,
Any 6-10 contiguous amino acids from antigenic site I,
Any 7-10 contiguous amino acids from antigenic site I,
Any 8-10 contiguous amino acids from antigenic site I,
Any 6 contiguous amino acids from antigenic site I,
Any 7 contiguous amino acids from antigenic site I,
Any 8 contiguous amino acids from antigenic site I,
Any 9 contiguous amino acids from antigenic site I,
Any 10 contiguous amino acids from antigenic site I,
Any 11 contiguous amino acids from antigenic site I,
Any 12 contiguous amino acids from antigenic site I.

The following specific sequences are used in VLPs according to the present invention:
From Peptide F (See FIG. 1 hereof):

```
        S10.1
                                           (SEQ ID NO: 8)
        LTNSELLSLI

S10.2
                                           (SEQ ID NO: 9)
        SELLSLINDM

S10.3
                                          (SEQ ID NO: 10)
        LSLINDMPIT

S10.4
                                          (SEQ ID NO: 11)
        INDMPITNDQ

S10.5
                                          (SEQ ID NO: 12)
        MPITNDQKKL

S10.6
                                          (SEQ ID NO: 13)
        TNDQKKLMSN

S10.7
                                          (SEQ ID NO: 14)
        DQKKLMSNNV
```

From Peptide G (See FIG. 1 hereof):

```
        G16
                                          (SEQ ID NO: 15)
        PCSICSNNPTCWAICK

G14
                                          (SEQ ID NO: 16)
        CSICSNNPTCWAIC

G12
                                          (SEQ ID NO: 17)
        SICSNNPTCWAI

G7
                                          (SEQ ID NO: 18)
        CSNNPTC

G5
                                          (SEQ ID NO: 19)
        SNNPT
```

Any one or more of the above epitopic peptides can be incorporated into VLPs according to the present invention in order to produce a vaccine against RSV infection or a RSV-related disorder.

Production of Virus-Like Particles

The present invention is directed to virus-like phage particles as well as methods for producing these particles in vivo or in vitro. The methods typically include producing virus-like particles (VLPs) and recovering the VLPs. As used herein, producing VLPs "in vitro" refers to producing VLPs outside of a cell, for instance, in a cell-free system, while producing virions "in vivo" refers to producing VLPs inside a cell, for instance, an *Eschericia coli* or *Pseudomonas aeruginosa* cell.

Bacteriophages

The single-strand RNA bacteriophages are a group of viruses found widely distributed in nature that infect diverse bacteria. These bacteriophages contain a single-stranded (+)-sense RNA genome, contain maturase, coat and replicase genes, and have small (<300 angstrom) icosahedral capsids. Members of this family include, but are not limited to, MS2, PP7, Qβ, R17, SP, PP7, GA, M11, MX1, f4, Cb5, Cb12r, Cb23r, 7s and f2 RNA bacteriophages.

Several phage in this family have been characterized in great detail in terms of genome sequence, molecular biology, and capsid structure and assembly. MS2 is perhaps the best studied member of the group. MS2 has a 3569-nucleotide single-strand RNA genome that encodes only four proteins: maturase, coat, lysis and replicase. The viral particle is comprised of 180 coat polypeptides, one molecule of maturase, and one copy of the RNA genome. In contrast to many other bacteriophages, the RNA phages are surprisingly simple. In fact, because the coat protein itself is responsible for formation of the icosahedral shell, the VLPs of this family of bacteriophage can be produced from plasmids as the product of a single gene (28). Likewise, PP7, a single-strand RNA bacteriophage of *Pseudomonas aeruginosa* and a distant relative to coliphages like MS2 and Qβ, may also be used in the present invention.

Examples of PP7 coat polypeptides include but are not limited to the various chains of PP7 Coat Protein Dimer in Complex With RNA Hairpin (e.g. Genbank Accession Nos. 2QUXR; 2QUXO; 2QUX_L; 2QUX_I; 2QUX_F; and 2QUX_C). See also Example 1 herein and (22). Examples of MS2 coat polypeptides include but are not limited to the Crystal Structure of MS2 coat protein (e.g. Genbank Accession Nos. 1MSCA; 1ZDIC; 1ZDIA; 1ZDIB; and 6MSFA). Other coat polypeptides are also useful in the present invention, as set forth hereinabove.

PP7 and MS2 Coat Polypeptides

The coat polypeptides useful in the present invention also include those having similarity with one or more of the coat polypeptide sequences disclosed above. The similarity is referred to as structural similarity. Structural similarity may be determined by aligning the residues of the two amino acid sequences (i.e., a candidate amino acid sequence and the amino acid sequence) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate amino acid sequence can be isolated from a single stranded RNA virus, or can be produced using recombinant techniques, or chemically or enzymatically synthesized. Preferably, two amino acid sequences are compared using the BESTFIT algorithm in the GCG package (version 10.2, Madison, Wis.), or the Blastp program of the BLAST 2 search algorithm available at http://www.ncbi.nlm.nih.gov/blast/b12seq/b12.html. Preferably, the default values for all BLAST 2 search parameters are used, including matrix=BLOSUM62; open gap penalty=11, extension gap penalty=1, gap xdropoff=50, expect=10, wordsize=3, and optionally, filter on. In the comparison of two amino acid sequences using the BLAST search algorithm, structural similarity is referred to as "identities." Preferably, a coat polypeptide also includes polypeptides with an amino acid sequence having at least 80% amino acid identity, at least 85% amino acid identity, at least 90% amino acid identity, or at least 95% amino acid identity to one or more of the amino acid sequences disclosed above. Preferably, a coat polypeptide is active. Whether a coat polypeptide is active can be determined by evaluating the ability of the polypeptide to form a capsid and package a single stranded RNA molecule. Such an evaluation can be done using an in vivo or in vitro system, and such methods are known in the art and routine. Alternatively, a polypeptide may be considered to be structurally similar if it has similar three-dimensional structure as the recited coat polypeptide and/or functional activity.

The RSV glycoprotein peptide sequences (e.g. the RSV F and G glycoprotein peptide sequences, preferably the F peptide sequences) may be present at the amino-terminal end of a coat polypeptide, at the carboxy-terminal end of a coat polypeptide, or it may be present elsewhere within the coat polypeptide. Preferably, the RSV glycoprotein peptide sequences (e.g. the RSV F and G glycoprotein peptide sequences, preferably the F peptide sequences) are present at a location in the coat polypeptide such that the insert sequence is expressed on the outer surface of the capsid. In a particular embodiment, RSV F and G glycoprotein peptide sequences (preferably F peptide sequences) may be inserted into the AB loop regions of the above-mentioned coat polypeptides. Examples of such locations include, for instance, insertion of the insert sequence into a coat polypeptide in accordance with the examples presented hereinafter.

Alternatively, the RSV glycoprotein peptide sequences (e.g. the RSV F and G glycoprotein peptide sequences, preferably the F peptide sequences) may be inserted at the N-terminus or C-terminus of the coat polypeptide.

The RSV glycoprotein peptide sequences (e.g. the RSV F and G glycoprotein peptide sequences, preferably the F peptide sequences) include but are not limited to amino acid sequences of, at least, three, five, ten, fifteen, twenty or thirty amino acids derived from the RSV F and G glycoprotein peptide sequences of RSV Types A and B.

In another particular embodiment, the RSV glycoprotein peptide sequence epitopes includes amino acid sequences with at least 75%, 80%, 85%, 90% or 95% homology to sequences derived from RSV Types A and B.

In order to determine a corresponding position in a structurally similar coat polypeptide, the amino acid sequence of this structurally similar coat polypeptide is aligned with the sequence of the named coat polypeptide as specified above.

In a particular embodiment, the coat polypeptide is a single-chain dimer containing an upstream and downstream subunit. Each subunit contains a functional coat polypeptide sequence. The RSV glycoprotein peptide sequences (e.g. the RSV Fund G glycoprotein peptide sequences, preferably F peptide sequences) may be inserted in the upstream and/or downstream subunit at the sites mentioned herein above, e.g., AB loop region of downstream subunit. In a particular embodiment, the coat polypeptide is a single chain dimer of a PP7 coat polypeptide.

Preparation of Transcription Unit

The transcription unit of the present invention comprises an expression regulatory region, (e.g., a promoter), a sequence encoding a coat polypeptide and transcription terminator. The RNA polynucleotide may optionally include a coat recognition site (also referred to a "packaging signal", "translational operator sequence", "coat recognition site"). Alternatively, the transcription unit may be free of the translational operator sequence. The promoter, coding region, transcription terminator, and, when present, the coat recognition site, are generally operably linked. "Operably linked" or "operably associated with" refer to a juxtaposition wherein the components so described are in a relationship permitting them to function in their intended manner. A regulatory sequence is "operably linked" to, or "operably associated with", a coding region when it is joined in such a way that expression of the coding region is achieved under conditions compatible with the regulatory sequence. The coat recognition site, when present, may be at any location within the RNA polynucleotide provided it functions in the intended manner.

The invention is not limited by the use of any particular promoter, and a wide variety of promoters are known. The promoter used in the invention can be a constitutive or an inducible promoter. Preferred promoters are able to drive high levels of RNA encoded by the coding region encoding the coat polypeptide Examples of such promoters are known in the art and include, for instance, the lac promoter, T7, T3, and SP6 promoters, among others.

The nucleotide sequences of the coding regions encoding coat polypeptides described herein are readily determined. These classes of nucleotide sequences are large but finite, and the nucleotide sequence of each member of the class can be readily determined by one skilled in the art by reference to the standard genetic code. Furthermore, the coding sequence of an RNA bacteriophage single chain coat polypeptide comprises a site for insertion of RSV glycoprotein peptide (e.g. the RSV F and G glycoprotein peptide and as otherwise described herein)-encoding sequences. In a particular embodiment, the site for insertion of the RSV glycoprotein peptide (e.g. the RSV F and G glycoprotein peptide)-encoding sequence is a restriction enzyme site.

In a particular embodiment, the coding region encodes a single-chain dimer of the coat polypeptide. In a most particular embodiment, the coding region encodes a modified single chain coat polypeptide dimer, where the modification comprises an insertion of a coding sequence at least four amino acids at the insertion site. The transcription unit may contain a bacterial promoter, such as a lac promoter or it may contain a bacteriophage promoter, such as a T7 promoter and optionally a T7 transcription terminator.

In addition to containing a promoter and a coding region encoding a fusion polypeptide, the RNA polynucleotide typically includes a transcription terminator, and optionally, a coat recognition site. A coat recognition site is a nucleotide sequence that forms a hairpin when present as RNA. This is also referred to in the art as a translational operator, a packaging signal, and an RNA binding site. Without intending to be limiting, this structure is believed to act as the binding site recognized by the translational repressor (e.g., the coat polypeptide), and initiate RNA packaging. The nucleotide sequences of coat recognition sites are known in the art. Other coat recognition sequences have been characterized in the single stranded RNA bacteriophages R17, GA, Qβ, SP, and PP7, and are readily available to the skilled person. Essentially any transcriptional terminator can be used in the RNA polynucleotide, provided it functions with the promoter. Transcriptional terminators are known to the skilled person, readily available, and routinely used.

Synthesis

As will be described in further detail below, the VLPs of the present invention may be produced in vivo by introducing transcription units into bacteria, especially if transcription units contain a bacterial promoter Alternatively VLPs synthesized in vitro in a coupled cell-free transcription/translation system.

Assembly of VLPs Encapsidating Heterologous Substances

As noted above, the VLPs of the present invention display a RSV glycoprotein peptide (e.g. the RSV F and G glycoprotein peptide) -encoding sequence. These VLPs may be assembled by performing an in vitro VLP assembly reaction. Specifically, purified coat protein subunits are obtained from VLPs that have been disaggregated with a denaturant (usually acetic acid). The protein subunits are mixed with a heterologous substance. In a particular embodiment, the substance has some affinity for the interior of the VLP and is preferably negatively charged. This substance could include an adjuvant, including, but not limited to RNA, bacterial DNA (CpG oligonucleotides), cholera toxin subunit B, or E. coli lymphotoxin, Synthesis In a particular embodiment, the populations of the present invention may be synthesized in a coupled in vitro transcription/translation system using procedures known in the art (see e.g. U.S. Pat. No. 7,008,651). In a particular embodiment, bacteriophage T7 (or a related) RNA polymerase is used to direct the high-level transcription of genes cloned under control of a T7 promoter in systems optimized to efficiently translate the large amounts of RNA thus produced.

Uses of VLPs and VLP Populations

There are a number of possible uses for the VLPs and VLP populations of the present invention. As will be described in further detail below, the VLPs may be used to as immunogenic compositions, particularly vaccines.

Immunogenic compositions

As noted above, the VLPs of the present invention may be used to formulate immunogenic compositions, particularly vaccines. The vaccines should be in a form that is capable of being administered to an animal. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition or disorder. Upon introduction into a host, the vaccine is able to provoke an immune response including, but not limited to, the production of antibodies and/or cytokines and/or the activation of cytotoxic T cells, antigen presenting cells, helper T cells, B cells, dendritic cells and/or other cellular responses.

Optionally, the vaccine of the present invention additionally includes an adjuvant which can be present in either a minor or major proportion relative to the compound of the present invention. The term "adjuvant" as used herein refers to non-specific stimulators of the immune response or substances that allow generation of a depot in the host which when combined with the vaccine of the present invention provide for an even more enhanced immune response. A variety of adjuvants can be used. Examples include complete and incomplete Freund's adjuvant, aluminum hydroxide, and modified muramyl dipeptide.

Optionally, the vaccine of the present invention additionally includes an adjuvant which can be present in either a minor or major proportion relative to the compound of the present invention.

EXAMPLES

The invention may be better understood by reference to the following non-limiting examples, which are provided as exemplary of the invention. The following examples are presented in order to more fully illustrate the preferred embodiments of the invention and should in no way be construed, however, as limiting the broad scope of the invention. References corresponding to numerical reference citations are listed after the examples.

Materials and Methods.

1. Plasmids.

Previously we described the construction of the expression plasmids pDSP62 and p2P7K32 (6). U.S. Provisional Patent Application Ser. Nos. 61/335,120, filed Dec. 31, 2009, 61/302,836, filed Feb. 9, 2010, 61/334,826, filed May 14, 2010, PCT application no. PCT/US2010/62638, filed 31 Dec. 2010 and PCT application no. PCT/US2011/24030, filed 8 Feb. 2011, all of which applications are incorporated by reference herein in their entirety. These plasmids code for the expression of a version of MS2 (pDSP1 or pDSP62) or PP7 (p2P7K32 or pDSP7) coat protein in which two copies of coat protein are genetically fused into a "single-chain" dimer. These plasmids also contain unique restriction sites that allow for genetic insertion of sequences into a region that encodes the AB-loop of the downstream copy of coat.

Details regarding these plasmids are presented below.

pDSP1—A Plasmid Expressing a Single-Chain Dimer with Convenient

Cloning Sites for Insertion in the AB-loop.

The plasmid pDSP1 (see FIGS. 3 and 4) contains the T7 transcription signals of pET3d and the kanamycin resistance and replication origin of pET9d. [Information regarding pET3d and pET9d may be found at the New England Biolabs vector database, https://www.lablife.org/ ct?f=v&a=listvecinfo). It expresses the coding sequence of the MS2 single-chain coat protein dimer (29), modified to contain unique SalI and KpnI restriction sites. This facilitates simple cloning of foreign sequences into the AB-loop. To make these sites unique, it was necessary to destroy other SalI and KpnI sites in the vector and in the upstream coat sequence.

The MS2 coat sequence (SEQ ID NO: 36) in the vicinity of the AB-loop insertion site for pDSP1 is shown below. Note the presence of SalI and KpnI sites.

```
  . . . 6  7  8  9  10 11 12 13 14 15 16 17 18 19 20 21 22 . . .

. . . GlnPheValLeuValAspAsnGlyGlyThrGlyAspValThrValAlaPro . . .

. . . CAGTTCGTTCTCGTCGACAATGGCGGTACCGGCGACGTGACTGTCGCCCA . . .
                  SalI       KpnI
```

With pDSP1, recombinant coat proteins are usually constructed by cloning into the AB-loop a PCR fragment generated using a monomeric coat protein sequence as template (e.g. pMCT). A synthetic oligonucleotide 5'-primer is designed to attach a SalI (or KpnI) site and a sequence of codons (corresponding to the insert sequence) to a site just upstream of the AB-loop (as shown in FIG. 1). A 3'-primer anneals to sequences in the plasmid vector just downstream of BamHI. The resulting PCR product is digested with SalI (or KpnI) and BamHI and cloned at the corresponding sites of pDSP1. This results in insertion of peptides into the AB-loop, the exact site of insertion depending on the specific design of the 5'-primer. For most insertions use of the SalI site is preferred as it affords more flexibility that KpnI in selection of the insertion site. FIG. 5 shows the nucleotide sequence of the plasmid pDSP62, which is similar to pDSP1 in that it serves as a vector for expression of a single-chain dimer form of the MS2 coat protein. In FIG. 5 the coat protein sequence has been modified so that a peptide derived from RSV F antigen (peptide S10.5, see FIG. 1) has been inserted into the downstream copy of coat protein at the AB-loop. A similar plasmid (pDSP7) has been designed to express a single-chain dimer version of the PP7 coat protein. This plasmid also allows for facile insertion of heterologous sequences into the PP7 AB-loop.

The Plasmid p2P7K32.

It should be noted that the three-dimensional structure of the PP7 capsid shows that it is comprised of a coat protein whose tertiary structure closely mimics that of MS2, even though the amino acid sequences of the two proteins show only about 12% sequence identity (33). The PP7 protein possesses an AB-loop into which peptides may be inserted following a scheme similar to the one we described previously for MS2 (30).

FIG. 6 depicts the p2P7K32 plasmid. This plasmid contains the lac promoter, an ampicillin resistance cassette, and the ColE1 replication origin. It expresses the coding sequence of the PP7 single-chain coat protein dimer modified to contain a unique KpnI restriction site only in the downstream copy of the coding sequence (5, 6). This modification resulted in the amino acid substitution E11T. In this design, heterologous peptides can be inserted at amino acid 11, but it should be noted that other specific insertion sites are possible, possibly anywhere within the AB-loop.

Recombinant MS2 and PP7 VLPs Displaying RSV Epitopes.

MS2 and PP7 coat protein single-chain dimers are highly tolerant of peptide insertions and produce correctly assembled VLPs displaying the peptide insertion on the surface of VLP in a highly dense, repetitive array. These VLPs are highly immunogenic and confer this high immunogenicity to heterologous peptides displayed on their surfaces. Here, we show the ability to make recombinant VLPs displaying RSV epitopes and show that these VLPs are highly immunogenic.

Example 1

Here we describe VLPs displaying a peptide antigens derived from RSV F and G glycoprotein peptides. To create the VLPs that display RSV peptides we designed oligonucleotide primers that allowed us to clone various RSV F- and G-derived sequences by PCR or primer extension into the AB-loop of either MS2 or PP7 coat. The predicted amino acid sequences of selected constructs are shown in FIG. 1. RSV sequences were selected as described below:

Targeting RSV F Protein.

A region of the RSV F glycoprotein mapping roughly to amino acids 252-272 has been identified as a major neutralizing epitope (23). Both MS2 and PP7 coat protein dimers can readily accept 10 amino acid insertions. Thus, we created a series of F protein chimeras in which linear 10 amino acid sequences were inserted into the downstream copy of the MS2 and PP7 single-chain dimers (shown in FIG. 1).

Targeting RSV G Protein.

Based on analysis of escape mutants, a region of RSV G glycoprotein between amino acids 164 and 197 is thought to be a major neutralizing epitope (24). Part of this region is fairly hydrophobic (aa 164-174) and it includes a pair of disulfide bonds forming a loop (between cysteines 173 and 186 and between cysteines 176 and 182). The region from aa 181-197 has a C3xC motif, the putative viral receptor binding region, has been used to generate antibodies, and is not hydrophobic in character. Thus, we have designed a series of constructs within this region that contain the cysteine loop plus flanking sequences or just the cysteine loop itself, as shown in FIG. 1.

The ability of recombinant coat proteins displaying RSV F and G sequences to form VLPs in lysates of cells expressing a peptide-coat protein recombinant was tested by electrophoresis on agarose gel of cells lysed by sonication. Ethidium bromide staining detects the RNA-containing VLP. Table 1 below shows the ability of recombinant MS2 and PP7 coat proteins to form VLPs. As shown, the vast majority of F and G recombinants resulted in VLPs.

TABLE 1

Ability of recombinant MS2 and PP7 coat proteins to form VLPs

| Insertion | MS2 | PP7 |
|---|---|---|
| G5 | +++[a] | +++ |
| G7 | +++ | +++ |
| G12 | + | ++ |
| G14 | - | + |
| G16 | - | + |
| 10.1 | + | nt[b] |
| 10.2 | + | nt |
| 10.3 | ++ | nt |
| 10.4 | +++ | nt |
| 10.5 | +++ | nt |
| 10.6 | +++ | nt |
| 10.7 | +++ | nt |

[a] +++ high yield of VLPs, ++ medium yield, + low yield, - no VLPs
[b] nt, Not Tested Example 2

RSV Peptides Displayed on MS2 VLPs Induce Antibodies that Bind to RSV Virions.

To test the immunogenicity of the VLPs, mice were immunized with selected recombinant MS2 VLPs by intramuscular injection. Groups of three Balb/c mice were immunized intramuscularly with 10 μg of VLPs plus incomplete Freunds Adjuvant (IFA). All mice were boosted with the same amount of VLPs at weeks 2 and 6. Sera were collected before each inoculation and weekly for three to four weeks after the boost. Sera from the mice were tested, by ELISA, for IgG antibodies specific for a peptide representing amino acids 252-272 from F protein or recombinant F protein, or for IgG antibodies specific for inactivated RSV virions (FIG. 2). As shown in FIGS. 2a and 2b, all of the F protein recombinant VLPs induced high-titer antibodies that bound to the synthetic F peptide and recombinant F protein. Three of the recombinant F VLPs (10.5, 10.6, & 10.7; FIG. 2c) and one of the recombinant G VLPs (G5; FIG. 2d) showed reactivity with RSV virions.

Summary of Experimental Results.

Genetic display of peptides on PP7 VLPs is well suited for the precise targeting of specific B-cell epitopes known to be the target of neutralizing antibodies. For many pathogens, including influenza (15, 32), Hepatitis C Virus (20), and HIV (4), the target epitopes of broadly neutralizing antibodies are poorly immunogenic, meaning that full-length proteins are inadequate for the induction of antibody responses by vaccination. On the other hand, the use of peptide epitopes as vaccines is limited because of their poor immunogenicity unless coupled to carrier proteins. The PP7 and MS2 VLP platforms that we have described allow for targeted introduction of specific peptide epitopes in a highly immunogenic context. Here, we show that MS2 and PP7 recombinant coat protein displaying the neutralizing epitopes derived from RSV G and F glycoproteins can form VLPs. VLPs displaying certain F and G epitopes induce antibodies that can bind to RSV virions. These recombinant VLPs can serve as a prophylactic vaccine for RSV infection.

REFERENCES

1. Bachmann, M. F., U. H. Rohrer, T. M. Kundig, K. Burki, H. Hengartner, and R. M. Zinkernagel. 1993. The influence of antigen organization on B cell responsiveness. Science 262:1448-1451.
2. Bachmann, M. F., and R. M. Zinkernagel. 1997. Neutralizing antiviral B cell responses. Annu Rev Immunol 15:235-70.
3. Brunswick, M., F. D. Finkelman, P. F. Highet, J. K. Inman, H. M. Dintzis, and J. J. Mond. 1988. Picogram quantities of anti-Ig antibodies coupled to dextran induce B cell proliferation. J Immunol 140:3364-72.
4. Burton, D. R., R. L. Stanfield, and I. A. Wilson. 2005. Antibody vs. HIV in a clash of evolutionary titans. Proc Natl Acad Sci U S A 102:14943-8.
5. Caldeira, J. C., and D. S. Peabody. 2007. Stability and assembly in vitro of bacteriophage PP7 virus-like particles. J Nanobiotechnology 5:10.
6. Caldeira Jdo, C., A. Medford, R. C. Kines, C. A. Lino, J. T. Schiller, B. Chackerian, and D. S. Peabody. 2010. Immunogenic display of diverse peptides, including a broadly cross-type neutralizing human papillomavirus L2 epitope, on virus-like particles of the RNA bacteriophage PP7. Vaccine 28:4384-93.
7. Chackerian, B., L. Briglio, P. S. Albert, D. R. Lowy, and J. T. Schiller. 2004. Induction of autoantibodies to CCR5 in macaques and subsequent effects upon challenge with an R5-tropic simian/human immunodeficiency virus. J Virol 78:4037-47.
8. Chackerian, B., M. R. Durfee, and J. T. Schiller. 2008. Virus-like display of a neo-self antigen reverses B cell anergy in a B cell receptor transgenic mouse model. J Immunol 180:5816-25.
9. Chackerian, B., D. R. Lowy, and J. T. Schiller. 2001. Conjugation of a self-antigen to papillomavirus-like particles allows for efficient induction of protective autoantibodies. J Clin Invest 108:415-23.
10. Chackerian, B., D. R. Lowy, and J. T. Schiller. 1999. Induction of autoantibodies to mouse CCR5 with recombinant papillomavirus particles. Proc. Natl. Acad. Sci. USA 96:2373-2378.
11. Chackerian, B., M. Rangel, Z. Hunter, and D. S. Peabody. 2006. Virus and virus-like particle-based immunogens for Alzheimer's disease induce antibody responses against amyloid-beta without concomitant T cell responses. Vaccine 24:6321-31.
12. Cornuz, J., S. Zwahlen, W. F. Jungi, J. Osterwalder, K. Klingler, G. van Melle, Y. Bangala, I. Guessous, P. Muller, J. Willers, P. Maurer, M. F. Bachmann, and T. Cerny. 2008. A vaccine against nicotine for smoking cessation: a randomized controlled trial. PLoS ONE 3:e2547.
13. Dintzis, H. M., R. Z. Dintzis, and B. Vogelstein. 1976. Molecular determinants of immunogenicity: the immunon model of immune response. Proc Natl Acad Sci U S A 73:3671-5.
14. Dintzis, R. Z., M. H. Middleton, and H. M. Dintzis. 1985. Inhibition of anti-DNP antibody formation by high doses of DNP-polyacrylamide molecules; effects of hapten density and hapten valence. J Immunol 135:423-7.
15. Ekiert, D. C., G. Bhabha, M. A. Elsliger, R. H. Friesen, M. Jongeneelen, M. Throsby, J. Goudsmit, and I. A. Wilson. 2009. Antibody recognition of a highly conserved influenza virus epitope. Science 324:246-51.

16. Fehr, T., D. Skrastina, P. Pumpens, and R. M. Zinkernagel. 1998. T cell-independent type I antibody response against B cell epitopes expressed repetitively on recombinant virus particles. Proc Natl Acad Sci U S A 95:9477-81.
17. Feldman, S. A., R. M. Hendry, and J. A. Beeler. 1999. Identification of a linear heparin binding domain for human respiratory syncytial virus attachment glycoprotein G. J Virol 73:6610-7.
18. Hall, C. B., E. E. Walsh, C. E. Long, and K. C. Schnabel. 1991. Immunity to and frequency of reinfection with respiratory syncytial virus. J Infect Dis 163:693-8.
19. Harro, C. D., Y. Y. Pang, R. B. Roden, A. Hildesheim, Z. Wang, M. J. Reynolds, T. C. Mast, R. Robinson, B. R. Murphy, R. A. Karron, J. Dillner, J. T. Schiller, and D. R. Lowy. 2001. Safety and immunogenicity trial in adult volunteers of a human papillomavirus 16 L1 virus-like particle vaccine. J Natl Cancer Inst 93:284-92.
20. Law, M., T. Maruyama, J. Lewis, E. Giang, A. W. Tarr, Z. Stamataki, P. Gastaminza, F. V. Chisari, I. M. Jones, R. I. Fox, J. K. Ball, J. A. McKeating, N. M. Kneteman, and D. R. Burton. 2008. Broadly neutralizing antibodies protect against hepatitis C virus quasispecies challenge. Nat Med 14:25-7.
21. Li, Q., C. Cao, B. Chackerian, J. Schiller, M. Gordon, K. E. Ugen, and D. Morgan. 2004. Overcoming antigen masking of anti-amyloidbeta antibodies reveals breaking of B cell tolerance by virus-like particles in amyloidbeta immunized amyloid precursor protein transgenic mice. BMC Neurosci 5:21.
22. Lim, F., and D. S. Peabody. 2002. RNA recognition site of PP7 coat protein. Nucleic Acids Res 30:4138-44.
23. Lopez, J. A., R. Bustos, C. Orvell, M. Berois, J. Arbiza, B. Garcia-Barreno, and J. A. Melero. 1998. Antigenic structure of human respiratory syncytial virus fusion glycoprotein. J Virol 72:6922-8.
24. Melero, J. A., B. Garcia-Barreno, I. Martinez, C. R. Pringle, and P. A. Cane. 1997. Antigenic structure, evolution and immunobiology of human respiratory syncytial virus attachment (G) protein. J Gen Virol 78 (Pt 10):2411-8.
25. Milich, D. R., M. Chen, F. Schodel, D. L. Peterson, J. E. Jones, and J. L. Hughes. 1997. Role of B cells in antigen presentation of the hepatitis B core. Proc Natl Acad Sci U S A 94:14648-53.
26. Olmsted, R. A., N. Elango, G. A. Prince, B. R. Murphy, P. R. Johnson, B. Moss, R. M. Chanock, and P. L. Collins. 1986. Expression of the F glycoprotein of respiratory syncytial virus by a recombinant vaccinia virus: comparison of the individual contributions of the F and G glycoproteins to host immunity. Proc Natl Acad Sci U S A 83:7462-6.
27. Olson, M. R., and S. M. Varga. 2008. Pulmonary immunity and immunopathology: lessons from respiratory syncytial virus. Expert Rev Vaccines 7:1239-55.
28. Peabody, D. S. 1990. Translational repression by bacteriophage MS2 coat protein expressed from a plasmid. A system for genetic analysis of a protein-RNA interaction. J Biol Chem 265:5684-9.
29. Peabody, D. S., and F. Lim. 1996. Complementation of RNA binding site mutations in MS2 coat protein heterodimers. Nucleic Acids Res 24:2352-9.
30. Peabody, D. S., B. Manifold-Wheeler, A. Medford, S. K. Jordan, J. do Carmo Caldeira, and B. Chackerian. 2008. Immunogenic display of diverse peptides on virus-like particles of RNA phage MS2. J Mol Biol 380:252-63.
31. Stott, E. J., G. Taylor, L. A. Ball, K. Anderson, K. K. Young, A. M. King, and G. W. Wertz. 1987. Immune and histopathological responses in animals vaccinated with recombinant vaccinia viruses that express individual genes of human respiratory syncytial virus. J Virol 61:3855-61.
32. Sui, J., W. C. Hwang, S. Perez, G. Wei, D. Aird, L. M. Chen, E. Santelli, B. Stec, G. Cadwell, M. Ali, H. Wan, A. Murakami, A. Yammanuru, T. Han, N. J. Cox, L. A. Bankston, R. O. Donis, R. C. Liddington, and W. A. Marasco. 2009. Structural and functional bases for broad-spectrum neutralization of avian and human influenza A viruses. Nat Struct Mol Biol 16:265-73.
33. Tars, K., K. Fridborg, M. Bundule, and L. Liljas. 2000. The three-dimensional structure of bacteriophage PP7 from Pseudomonas aeruginosa at 3.7-A resolution. Virology 272:331-7.
34. Thyagarajan, R., N. Arunkumar, and W. Song. 2003. Polyvalent antigens stabilize B cell antigen receptor surface signaling microdomains. J Immunol 170:6099-106.
35. Tissot, A. C., P. Maurer, J. Nussberger, R. Sabat, T. Pfister, S. Ignatenko, H. D. Volk, H. Stocker, P. Muller, G. T. Jennings, F. Wagner, and M. F. Bachmann. 2008. Effect of immunisation against angiotensin II with CYT006-AngQb on ambulatory blood pressure: a double-blind, randomised, placebo-controlled phase IIa study. Lancet 371:821-7.
36. Zhang, L. F., J. Zhou, S. Chen, L. L. Cai, Q. Y. Bao, F. Y. Zheng, J. Q. Lu, J. Padmanabha, K. Hengst, K. Malcolm, and I. H. Frazer. 2000. HPV6b virus like particles are potent immunogens without adjuvant in man. Vaccine 18:1051-8.

What is claimed is:

1. An immunogenic RNA bacteriophage virus-like particle (VLP) comprising an RNA bacteriophage single chain coat polypeptide dimer comprising (i) an upstream coat protein subunit, (ii) a downstream coat protein subunit, and (iii) a heterologous Respiratory Syncytial Virus (RSV) glycoprotein F peptide of 5 to 27 amino acids that consists of a contiguous amino acid sequence of SEQ ID NO: 5.

2. The RNA bacteriophage VLP of claim 1, wherein that VLP is a PP7 or MS2 VLP.

3. The RNA bacteriophage VLP of claim 1, wherein the RSV peptide is inserted at the amino terminus of the single chain dimer polypeptide.

4. The RNA bacteriophage VLP of claim 1, wherein the RSV peptide is inserted in the AB loop of the downstream subunit.

* * * * *

SEQUENCE LISTING

```
<160> NUMBER OF SEQ ID NOS: 54

<210> SEQ ID NO 1
<211> LENGTH: 5096
<212> TYPE: DNA
<213> ORGANISM: Artificial Sequence
<220> FEATURE:
<223> OTHER INFORMATION: pDSP1 SEQUENCE

<400> SEQUENCE: 1
ttcttagaaa aactcatcga gcatcaaatg aaactgcaat ttattcatat caggattatc      60
aataccatat ttttgaaaaa gccgtttctg taatgaagga gaaaactcac cgaggcagtt     120
ccataggatg gcaagatcct ggtatcggtc tgcgattccg actcgtccaa catcaataca     180
```

```
acctattaat ttcccctcgt caaaaataag gttatcaagt gagaaatcac catgagtgac    240
gactgaatcc ggtgagaatg gcaaaagctt atgcatttct ttccagactt gttcaacagg    300
ccagccatta cgctcgtcat caaaatcact cgcatcaacc aaaccgttat tcattcgtga    360
ttgcgcctga gcgagacgaa atacgcgatc gctgttaaaa ggacaattac aaacaggaat    420
cgaatgcaac cggcgcagga acactgccag cgcatcaaca atattttcac ctgaatcagg    480
atattcttct aatacctgga atgctgtttt cccggggatc gcagtggtga gtaaccatgc    540
atcatcagga gtacggataa aatgcttgat ggtcggaaga ggcataaatt ccgtcagcca    600
gtttagtctg accatctcat ctgtaacatc attggcaacg ctaccttttgc catgtttcag   660 aaacaactct ggcgcatcgg gcttcccata caatcgatag attgtcgcac ctgattgccc    720
gacattatcg cgagcccatt tatacccata taaatcagca tccatgttgg aatttaatcg    780
cggcctcgag caagacgttt cccgttgaat atggctcata cacccccttg tattactgtt    840
tatgtaagca gacagttttta ttgttcatga ccaaaatccc ttaacgtgag ttttcgttcc    900
actgagcgtc agaccccgta gaaaagatca aggatcttc ttgagatcct ttttttctgc     960
gcgtaatctg ctgcttgcaa acaaaaaaac caccgctacc agcggtggtt tgtttgccgg   1020
atcaagagct accaactctt tttccgaagg taactggctt cagcagagcg cagataccaa   1080
atactgtcct tctagtgtag ccgtagttag gccaccactt caagaactct gtagcaccgc   1140
ctacatacct cgctctgcta atcctgttac cagtggctgc tgccagtggc gataagtcgt   1200
gtcttaccgg gttggactca agacgatagt taccggataa ggcgcagcgg tcgggctgaa   1260
cggggggttc gtgcacacag cccagcttgg agcgaacgac ctacaccgaa ctgagatacc   1320
tacagcgtga gctatgagaa agcgccacgc ttcccgaagg gagaaaggcg gacaggtatc   1380
cggtaagcgg cagggtcgga acaggagagc gcacgaggga gcttccaggg ggaaacgcct   1440
ggtatcttta tagtcctgtc gggtttcgcc acctctgact tgagcgtcga ttttttgtgat  1500 gctcgtcagg ggggcggagc ctatggaaaa acgccagcaa cgcggccttt ttacggttcc   1560
tggccttttg ctggccttttt gctcacatgt tctttcctgc gttatcccct gattctgtgg   1620
ataaccgtat taccgccttt gagtgagctg ataccgctcg ccgcagccga acgaccgagc   1680
gcagcgagtc agtgagcgag gaagcggaag agcgcctgat gcggtatttt ctccttacgc   1740
atctgtgcgg tatttcacac cgcatatatg gtgcactctc agtacaatct gctctgatgc   1800
cgcatagtta agccagtata cactccgcta tcgctacgtg actgggtcat ggctgcgccc   1860
cgacacccgc caacacccgc tgacgcgccc tgacgggctt gtctgctccc ggcatccgct   1920
tacagacaag ctgtgaccgt ctccgggagc tgcatgtgtc agaggttttc accgtcatca   1980
ccgaaacgcg cgaggcagct gcggtaaagc tcatcagcgt ggtcgtgaag cgattcacag   2040
atgtctgcct gttcatccgc gtccagctcg ttgagtttct ccagaagcgt taatgtctgg   2100
cttctgataa agcgggccat gttaaggcg gttttttcct gtttggtcac tgatgcctcc    2160
gtgtaagggg gatttctgtt catgggggta atgataccga tgaaacgaga gaggatgctc   2220
acgatacggg ttactgatga tgaacatgcc cggttactgg aacgttgtga gggtaaacaa   2280
ctggcggtat ggatgcggcg ggaccagaga aaaatcactc agggtcaatg ccagcgcttc   2340
gttaatacag atgtaggtgt tccacagggt agccagcagc atcctgcgat gcagatccgg   2400
aacataatgg tgcagggcgc tgacttccgc gtttccagac tttacgaaac acggaaaccg   2460
aagaccattc atgttgttgc tcaggtcgca gacgttttgc agcagcagtc gcttcacgtt   2520
```

```
cgctcgcgta tcggtgattc attctgctaa ccagtaaggc aaccccgcca gcctagccgg    2580
gtcctcaacg acaggagcac gatcatgcgc acccgtggcc aggacccaac gctgcccgag    2640
atgcgccgcg tgcggctgct ggagatggcg gacgcgatgg atatgttctg ccaagggttg    2700
gtttgcgcat tcacagttct ccgcaagaat tgattggctc caattcttgg agtggtgaat    2760
ccgttagcga ggtgccgccg gcttccattc aggtcgaggt ggcccggctc catgcaccgc    2820
gacgcaacgc ggggaggcag acaaggtata gggcggcgcc tacaatccat gccaacccgt    2880
tccatgtgct cgccgaggcg gcataaatcg ccgtgacgat cagcggtcca gtgatcgaag    2940
ttaggctggt aagagccgcg agcgatcctt gaagctgtcc ctgatggtcg tcatctacct    3000
gcctggacag catggcctgc aacgcgggca tcccgatgcc gccggaagcg agaagaatca    3060
taatggggaa ggccatccag cctcgcgtcg cgaacgccag caagacgtag cccagcgcgt    3120
cggccgccat gccggcgata atggcctgct tctcgccgaa acgtttggtg gcgggaccag    3180
tgacgaaggc ttgagcgagg gcgtgcaaga ttccgaatac cgcaagcgac aggccgatca    3240
tcgtcgcgct ccagcgaaag cggtcctcgc cgaaaatgac ccagagcgct gccggcacct    3300
gtcctacgag ttgcatgata aagaagacag tcataagtgc ggcgacgata gtcatgcccc    3360
gcgcccaccg gaaggagctg actgggttga aggctctcaa gggcatcggc tctcccttat    3420
gcgactcctg cattaggaag cagcccagta gtaggttgag gccgttgagc accgccgccg    3480
caaggaatgg tgcatgcaag gagatggcgc ccaacagtcc cccggccacg gggcctgcca    3540
ccatacccac gccgaaacaa gcgctcatga gcccgaagtg gcgagcccga tcttccccat    3600
cggtgatgtc ggcgatatag gcgccagcaa ccgcacctgt ggcgcggtg atgccggcca    3660 cgatgcgtcc ggcgtagagg atcgagatct cgatcccgcg aaattaatac gactcactat    3720
agggagacca caacggtttc cctctagaaa taattttgtt taactttaag aaggagatat    3780
accatggctt ctaactttac tcagttcgtt ctcgttgaca atggcggaac tggcgacgtg    3840
actgtcgccc caagcaactt cgctaacggg gtcgctgaat ggatcagctc taactcgcgt    3900
tcacaggctt acaaagtaac ctgtagcgtt cgtcagagct ctgcgcagaa tcgcaaatac    3960
accatcaaag tcgaggtgcc taaagtggca acccagactg ttggtggtgt agagcttcct    4020
gtagccgcat ggcgttcgta cttaaatatg gaactaacca ttccaatttt cgctacgaat    4080
tccgactgcg agcttattgt taaggcaatg caaggtctcc taaagatgg aaacccgatt    4140 ccctcagcaa tcgcagcaaa ctccggcctc tacggcaact ttactcagtt cgttctcgtc    4200
gacaatggcg gtaccggcga cgtgactgtc gccccaagca acttcgctaa cggggtcgct    4260
gaatggatca gctctaactc gcgttcacag gcttacaaag taacctgtag cgttcgtcag    4320
agctctgcgc agaatcgcaa atacaccatc aaagtcgagg tgcctaaagt ggcaacccag    4380
actgttggtg gtgtagagct tcctgtagcc gcatggcgtt cgtacttaaa tatgaaacta    4440
accattccaa ttttcgctac gaattccgac tgcgagctta ttgttaaggc aatgcaaggt    4500
ctcctaaaag atggaaaccc gattccctca gcaatcgcag caaactccgg catctactaa    4560
tagacgccgg gttaattaat taaggatccg gctgctaaca aagcccgaaa ggaagctgag    4620
ttggctgctg ccaccgctga gcaataacta gcataacccc ttggggcctc taaacgggtc    4680
ttgaggggtt ttttgctgaa aggaggaact atatccggat atccacagga cgggtgtggt    4740
cgccatgatc gcgtagtcga tagtggctcc aagtagcgaa gcgagcagga ctgggcggcg    4800
gccaaagcgg tcggacagtg ctccgagaac gggtgcgcat agaaattgca tcaacgcata    4860
tagcgctagc agcacgccat agtgactggc gatgctgtcg gaatggacga tatcccgcaa    4920
```
gaggcccggc agtaccggca taaccaagcc tatgcctaca gcatccaggg tgacggtgcc 4980
gaggatgacg atgagcgcat tgttagattt catacacggt gcctgactgc gttagcaatt 5040
taactgtgat aaactaccgc attaaagctt atcgatgata agctgtcaaa catgaa 5096

<210> SEQ ID NO 2
<211> LENGTH: 4510
<212> TYPE: DNA
<213> ORGANISM: Artificial Sequence
<220> FEATURE:
<223> OTHER INFORMATION: pDSP62 SEQUENCE containing F antigen peptide S10.5 inserted into the AB-loop of one copy of the single-chain dimer.

<400> SEQUENCE: 2
ttcttagaaa aactcatcga gcatcaaatg aaactgcaat ttattcatat caggattatc 60
aataccatat ttttgaaaaa gccgtttctg taatgaagga gaaaactcac cgaggcagtt 120
ccataggatg gcaagatcct ggtatcggtc tgcgattccg actcgtccaa catcaataca 180
acctattaat ttcccctcgt caaaaataag gttatcaagt gagaaatcac catgagtgac 240
gactgaatcc ggtgagaatg gcaaaagctt atgcatttct ttccagactt gttcaacagg 300
ccagccatta cgctcgtcat caaaatcact cgcatcaacc aaaccgttat tcattcgtga 360
ttgcgcctga gcgagacgaa atacgcgatc gctgttaaaa ggacaattac aaacaggaat 420
cgaatgcaac cggcgcagga acactgccag cgcatcaaca atattttcac ctgaatcagg 480
atattcttct aatacctgga atgctgtttt cccggggatc gcagtggtga gtaaccatgc 540
atcatcagga gtacggataa aatgcttgat ggtcggaaga ggcataaatt ccgtcagcca 600
gtttagtctg accatctcat ctgtaacatc attggcaacg ctacctttgc catgtttcag 660
aaacaactct ggcgcatcgg gcttcccata caatcgatag attgtcgcac ctgattgccc 720
gacattatcg cgagcccatt tatacccata taaatcagca tccatgttgg aatttaatcg 780
cggcctcgag caagacgttt cccgttgaat atggctcata acaccccttg tattactgtt 840
tatgtaagca gacagtttta ttgttcatga ccaaaatccc ttaacgtgag ttttcgttcc 900
actgagcgtc agaccccgta gaaaagatca aaggatcttc ttgagatcct ttttttctgc 960
gcgtaatctg ctgcttgcaa acaaaaaaac caccgctacc agcggtggtt tgtttgccgg 1020
atcaagagct accaactctt tttccgaagg taactggctt cagcagagcg cagataccaa 1080
atactgtcct tctagtgtag ccgtagttag gccaccactt caagaactct gtagcaccgc 1140
ctacatacct cgctctgcta atcctgttac cagtggctgc tgccagtggc gataagtcgt 1200
gtcttaccgg gttggactca agacgatagt taccggataa ggcgcagcgg tcgggctgaa 1260
cggggggttc gtgcacacag cccagcttgg agcgaacgac ctacaccgaa ctgagatacc 1320
tacagcgtga gctatgagaa agcgccacgc ttcccgaagg gagaaaggcg gacaggtatc 1380
cggtaagcgg cagggtcgga acaggagagc gcacgaggga gcttccaggg ggaaacgcct 1440
ggtatcttta tagtcctgtc gggtttcgcc acctctgact tgagcgtcga tttttgtgat 1500
gctcgtcagg ggggcggagc ctatggaaaa acgccagcaa cgcggccttt ttacggttcc 1560
tggccttttg ctggcctttt gctcacatgt tctttcctgc gttatcccct gattctgtgg 1620
ataaccgtat taccgccttt gagtgagctg ataccgctcg ccgcagccga acgaccgagc 1680
gcagcgagtc agtgagcgag gaagcggaag agcgcctgat gcggtatttt ctccttacgc 1740
atctgtgcgg tatttcacac cgcatatatg gtgcactctc agtacaatct gctctgatgc 1800

```
cgcatagtta agccagtata cactccgcta tcgctacgtg actgggtcat ggctgcgccc   1860
cgacacccgc caacacccgc tgacgcgccc tgacgggctt gtctgctccc ggcatccgct   1920
tacagacaag ctgtgaccgt ctccgggagc tgcatgtgtc agaggttttc accgtcatca   1980
ccgaaacgcg cgaggcagct gcggtaaagc tcatcagcgt ggtcgtgaag cttttcaaaa   2040
ttgtaaacgt taatattttg ttaaaattcg cgttaaattt ttgttaaatc agctcatttt   2100
ttaaccaata ggccgaaatc ggcaaaatcc cttataaatc aaaagaatag cccgagatag   2160
ggttgagtgt tgttccagtt tggaacaaga gtccactatt aaagaacgtg gactccaacg   2220
tcaaagggcg aaaaaccgtc tatcagggcg atggcccact acgtgaacca tcacccaaat   2280
caagtttttg gggtcgaggt gccgtaaagc actaaatcgg aaccctaaag ggagcccccg   2340
atttagagct tgacggggaa agccggcgaa cgtggcgaga aaggaaggga agaaagcgaa   2400
aggagcgggc gctagggcgc tggcaagtgt agcggtcacg ctgcgcgtaa ccaccacacc   2460
cgccgcgctt aatgcgccgc tacagggcgc gtactatggt tgctttgacg tcggccgcca   2520
tgccggcgat aatggcctgc ttctcgccga aacgtttggt ggcgggacca gtgacgaagg   2580
cttgagcgag ggcgtgcaag attccgaata ccgcaagcga caggccgatc atcgtcgcgc   2640
tccagcgaaa gcggtcctcg ccgaaaatga cccagagcgc tgccggcacc tgtcctacga   2700
gttgcatgat aaagaagaca gtcataagtg cggcgacgat agtcatgccc cgcgcccacc   2760
ggaaggagct gactggggttg aaggctctca agggcatcgg ctctccctta tgcgactcct   2820
gcattaggaa gcagcccagt agtaggttga ggccgttgag caccgccgcc gcaaggaatg   2880
gtgcatgcaa ggagatggcg cccaacagtc ccccggccac ggggcctgcc accatacccca   2940
cgccgaaaca agcgctcatg agcccgaagt ggcgagcccg atcttcccca tcggtgatgt   3000
cggcgatata ggcgccagca accgcacctg tggcgccggt gatgccggcc acgatgcgtc   3060
cggcgtagag gatcgagatc tcgatcccgc gaaattaata cgactcacta tagggagacc   3120
acaacggttt ccctctagaa ataattttgt ttaactttaa gaaggagata taccatggca   3180
agcaatttca cgcaatttgt attggtagat aacgggggta cggggggatgt tacggtagca   3240
ccttcaaatt ttgcaaatgg tgtagcagag tggatatcaa gcaatagcag aagccaagca   3300
tataaggtta cgtgctcagt aagacaatca agcgctcaaa acagaaagta tacgataaag   3360
gtagaagttc cgaaggttgc tacgcaaacg gtaggtggtg ttgaattgcc ggttgcagct   3420
tggagaagct atctcaacat ggagttgacg ataccctatat ttgcaaccaa cagtgattgt   3480
gaattgatag taaaagctat gcaggggttg ttgaaggacg gtaatcctat accgagcgct   3540
atagctgcta atagtggcct ctacggcaac tttactcagt tcgttctcgt cgacaatggc   3600
atgccgatca ccaacgacca gaaaaaactg ggcgacgtga ctgtcgcccc aagcaacttc   3660
gctaacgggg tcgctgaatg gatcagctct aactcgcgtt cacaggctta caaagtaacc   3720
tgtagcgttc gtcagagctc tgcgcagaat cgcaaataca ccatcaaagt cgaggtgcct   3780
aaagtggcaa cccagactgt tggtggtgta gagcttcctg tagccgcatg gcgttcgtac   3840
ttaaatatgg aactaaccat tccaattttc gctacgaatt ccgactgcga gcttattgtt   3900
aaggcaatgc aaggtctcct aaaagatgga aacccgattc cctcagcaat cgcagcaaac   3960
tccggcatct actaatagac gccgggttaa ttaattagga tccggctgct aacaaagccc   4020
gaaaggaagc tgagttggct gctgccaccg ctgagcaata actagcataa cccccttgggg   4080
cctctaaacg ggtcttgagg ggttttttgc tgaaaggagg aactatatcc ggatatccac   4140
aggacgggtg tggtcgccat gatcgcgtag tcgatagtgg ctccaagtag cgaagcgagc   4200
```
aggactgggc ggcggccaaa gcggtcggac agtgctccga gaacgggtgc gcatagaaat 4260
tgcatcaacg catatagcgc tagcagcacg ccatagtgac tggcgatgct gtcggaatgg 4320
acgatatccc gcaagaggcc cggcagtacc ggcataacca agcctatgcc tacagcatcc 4380
agggtgacgg tgccgaggat gacgatgagc gcattgttag atttcataca cggtgcctga 4440
ctgcgttagc aatttaactg tgataaacta ccgcattaaa gcttatcgat gataagctgt 4500
caaacatgaa 4510

<210> SEQ ID NO 3
<211> LENGTH: 20
<212> TYPE: DNA
<213> ORGANISM: Artificial Sequence
<220> FEATURE:
<223> OTHER INFORMATION: 3' (reverse)-primer

<400> SEQUENCE: 3
cgggctttgt tagcagccgg 20

<210> SEQ ID NO 4
<211> LENGTH: 574
<212> TYPE: PRT
<213> ORGANISM: respiratory syncytial virus

<400> SEQUENCE: 4

Met Glu Leu Pro Ile Leu Lys Ala Asn Ala Ile Thr Thr Ile Leu Ala
1 5 10 15

Ala Val Thr Phe Cys Phe Ala Ser Ser Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Met Lys
65 70 75 80

Gln Glu Leu Asp Lys Tyr Lys Asn Ala Val Thr Glu Leu Gln Leu Leu
85 90 95

Met Gln Ser Thr Pro Ala Ala Asn Asn Arg Ala Arg Arg Glu Leu Pro
100 105 110

Arg Phe Met Asn Tyr Thr Leu Asn Asn Thr Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Ile Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Arg Ser Cys Arg Ile Ser Asn Ile Glu Thr Val Ile Glu Phe Gln
210 215 220

His Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu

```
            245                 250                 255
Leu Leu Ser Leu Ile Asn Asp Met Pro Ile Thr Asn Asp Gln Lys Lys
        260                 265                 270

Leu Met Ser Asn Asn Val Gln Ile Val Arg Gln Gln Ser Tyr Ser Ile
    275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
        340                 345                 350

Pro Gln Ala Glu Thr Cys Lys Val Gln Ser Asn Arg Val Phe Cys Asp
    355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Gly Lys Ser Thr Thr Asn Ile Met Ile Thr
    515                 520                 525

Thr Ile Ile Ile Glu Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570
```

<210> SEQ ID NO 5
<211> LENGTH: 27
<212> TYPE: PRT
<213> ORGANISM: Artificial Sequence
<220> FEATURE:
<223> OTHER INFORMATION: antigenic site II

<400> SEQUENCE: 5

```
Leu Thr Asn Ser Glu Leu Leu Ser Leu Ile Asn Asp Met Pro Ile Thr
1               5                   10                  15

Asn Asp Gln Lys Lys Leu Met Ser Asn Asn Val
            20                  25
```

```
<210> SEQ ID NO 6
<211> LENGTH: 20
<212> TYPE: PRT
<213> ORGANISM: Artificial Sequence
<220> FEATURE:
<223> OTHER INFORMATION: antigenic site IV

<400> SEQUENCE: 6

Lys Cys Thr Ala Ser Asn Lys Asn Arg Gly Ile Ile Lys Thr Phe Ser
1               5                   10                  15

Asn Gly Cys Asp
            20

<210> SEQ ID NO 7
<211> LENGTH: 20
<212> TYPE: PRT
<213> ORGANISM: Artificial Sequence
<220> FEATURE:
<223> OTHER INFORMATION: antigenic site I

<400> SEQUENCE: 7

Leu Cys Asn Val Asp Ile Phe Asn Pro Lys Tyr Asp Cys Lys Ile Met
1               5                   10                  15

Thr Ser Lys Thr
            20

<210> SEQ ID NO 8
<211> LENGTH: 10
<212> TYPE: PRT
<213> ORGANISM: Artificial Sequence
<220> FEATURE:
<223> OTHER INFORMATION: S10.1 sequence  used in VLPs from peptide F

<400> SEQUENCE: 8

Leu Thr Asn Ser Glu Leu Leu Ser Leu Ile
1               5                   10

<210> SEQ ID NO 9
<211> LENGTH: 10
<212> TYPE: PRT
<213> ORGANISM: Artificial Sequence
<220> FEATURE:
<223> OTHER INFORMATION: S10.2 sequence used in VLPs from peptide F

<400> SEQUENCE: 9

Ser Glu Leu Leu Ser Leu Ile Asn Asp Met
1               5                   10

<210> SEQ ID NO 10
<211> LENGTH: 10
<212> TYPE: PRT
<213> ORGANISM: Artificial Sequence
<220> FEATURE:
<223> OTHER INFORMATION: S10.3 sequence used in VLPs from peptide F

<400> SEQUENCE: 10

Leu Ser Leu Ile Asn Asp Met Pro Ile Thr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: S10.4 sequence used in VLPs from peptide F

<400> SEQUENCE: 11
```

Ile Asn Asp Met Pro Ile Thr Asn Asp Gln
1               5                   10

<210> SEQ ID NO 12
<211> LENGTH: 10
<212> TYPE: PRT
<213> ORGANISM: Artificial Sequence
<220> FEATURE:
<223> OTHER INFORMATION: S10.5 sequence used in VLPs from peptide F

<400> SEQUENCE: 12

Met Pro Ile Thr Asn Asp Gln Lys Lys Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: S10.6 sequence used in VLPs from peptide F

<400> SEQUENCE: 13

Thr Asn Asp Gln Lys Lys Leu Met Ser Asn
1               5                   10

<210> SEQ ID NO 14
<211> LENGTH: 10
<212> TYPE: PRT
<213> ORGANISM: Artificial Sequence
<220> FEATURE:
<223> OTHER INFORMATION: S10.7 sequence used in VLPs from peptide F

<400> SEQUENCE: 14

Asp Gln Lys Lys Leu Met Ser Asn Asn Val
1               5                   10

<210> SEQ ID NO 15
<211> LENGTH: 16
<212> TYPE: PRT
<213> ORGANISM: Artificial Sequence
<220> FEATURE:
<223> OTHER INFORMATION: G16 sequence used in VLPs from peptide G

<400> SEQUENCE: 15

Pro Cys Ser Ile Cys Ser Asn Asn Pro Thr Cys Trp Ala Ile Cys Lys
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: G14 sequence used in VLPs from peptide G

<400> SEQUENCE: 16

Cys Ser Ile Cys Ser Asn Asn Pro Thr Cys Trp Ala Ile Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: G12 sequence used in VLPs from peptide G

<400> SEQUENCE: 17

-continued

```
Ser Ile Cys Ser Asn Asn Pro Thr Cys Trp Ala Ile
1               5                   10
```

<210> SEQ ID NO 18
<211> LENGTH: 7
<212> TYPE: PRT
<213> ORGANISM: Artificial Sequence
<220> FEATURE:
<223> OTHER INFORMATION: G7 sequence used in VLPs from peptide G

<400> SEQUENCE: 18

```
Cys Ser Asn Asn Pro Thr Cys
1               5
```

<210> SEQ ID NO 19
<211> LENGTH: 5
<212> TYPE: PRT
<213> ORGANISM: Artificial Sequence
<220> FEATURE:
<223> OTHER INFORMATION: G5 sequence used in VLPs from peptide G

<400> SEQUENCE: 19

```
Ser Asn Asn Pro Thr
1               5
```

<210> SEQ ID NO 20
<211> LENGTH: 102
<212> TYPE: DNA
<213> ORGANISM: Artificial Sequence
<220> FEATURE:
<223> OTHER INFORMATION: DNA sequence of RSV G protein target region

<400> SEQUENCE: 20

```
cacttcgaag ttttcaactt cgttccgtgc tctatctgct ctaacaaccc gacctgctgg      60
gctatctgca aacgtatccc gaacaaaaaa ccgggtaaaa aa                        102
```

<210> SEQ ID NO 21
<211> LENGTH: 54
<212> TYPE: DNA
<213> ORGANISM: Artificial Sequence
<220> FEATURE:
<223> OTHER INFORMATION: p2P7K32 (PP7) (KpnI site) DNA sequence of
      downstream copy of coat protein.

<400> SEQUENCE: 21

```
atggccaaaa ccatcgttct ttcggtcggt accgctactc gcactctgac tgag            54
```

<210> SEQ ID NO 22
<211> LENGTH: 51
<212> TYPE: DNA
<213> ORGANISM: Artificial Sequence
<220> FEATURE:
<223> OTHER INFORMATION: pDSP1 (MS2) (SalI) restriction site sequence
      of the downstream copy of coat protein.

<400> SEQUENCE: 22

```
gctaacttta tcagttcgt tctcgtcgac aatggcggta ccggcgacgt g               51
```

<210> SEQ ID NO 23
<211> LENGTH: 66
<212> TYPE: DNA
<213> ORGANISM: Artificial Sequence
<220> FEATURE:
<223> OTHER INFORMATION: S10.1 restriction site

<400> SEQUENCE: 23
gttctcgtcg acaatggcct gaccaactct gaactgctgt ctctgatcgg cgacgtgact    60
gtcgcc                                                              66

<210> SEQ ID NO 24
<211> LENGTH: 66
<212> TYPE: DNA
<213> ORGANISM: Artificial Sequence
<220> FEATURE:
<223> OTHER INFORMATION: S10.2 restriction site

<400> SEQUENCE: 24
gttctcgtcg acaatggctc tgaactgctg tctctgatca acgacatggg cgacgtgact    60
gtcgcc                                                              66

<210> SEQ ID NO 25
<211> LENGTH: 66
<212> TYPE: DNA
<213> ORGANISM: Artificial Sequence
<220> FEATURE:
<223> OTHER INFORMATION: S10.3 restriction site

<400> SEQUENCE: 25
gttctcgtcg acaatggcct gtctctgatc aacgacatgc cgatcaccgg cgacgtgact    60
gtcgcc                                                              66

<210> SEQ ID NO 26
<211> LENGTH: 66
<212> TYPE: DNA
<213> ORGANISM: Artificial Sequence
<220> FEATURE:
<223> OTHER INFORMATION: S10.4 restriction site

<400> SEQUENCE: 26
gttctcgtcg acaatggcat caacgacatg ccgatcacca acgaccaggg cgacgtgact    60
gtcgcc                                                              66

<210> SEQ ID NO 27
<211> LENGTH: 66
<212> TYPE: DNA
<213> ORGANISM: Artificial Sequence
<220> FEATURE:
<223> OTHER INFORMATION: S10.5 restriction site

<400> SEQUENCE: 27
gttctcgtcg acaatggcat gccgatcacc aacgaccaga aaaaactggg cgacgtgact    60
gtcgcc                                                              66

<210> SEQ ID NO 28
<211> LENGTH: 66
<212> TYPE: DNA
<213> ORGANISM: Artificial Sequence
<220> FEATURE:
<223> OTHER INFORMATION: S10.6 restriction site

<400> SEQUENCE: 28
gttctcgtcg acaatggcac caacgaccag aaaaaactga tgtctaacgg cgacgtgact    60
gtcgcc                                                              66

<210> SEQ ID NO 29
<211> LENGTH: 66
<212> TYPE: DNA
<213> ORGANISM: Artificial Sequence
<220> FEATURE:
<223> OTHER INFORMATION: S10.7 restriction site

<400> SEQUENCE: 29
gttctcgtcg acaatggcga ccagaaaaaa ctgatgtcta acaacgttgg cgacgtgact    60
gtcgcc    66

<210> SEQ ID NO 30
<211> LENGTH: 102
<212> TYPE: DNA
<213> ORGANISM: Artificial Sequence
<220> FEATURE:
<223> OTHER INFORMATION: primer for G peptide insertion

<400> SEQUENCE: 30
cacttcgaag ttttcaactt cgttccgtgc tctatctgct ctaacaaccc gacctgctgg    60
gctatctgca aacgtatccc gaacaaaaaa ccgggtaaaa aa    102

<210> SEQ ID NO 31
<211> LENGTH: 84
<212> TYPE: DNA
<213> ORGANISM: Artificial Sequence
<220> FEATURE:
<223> OTHER INFORMATION: primer for G16 peptide insertion

<400> SEQUENCE: 31
gttctcgtcg acaatggccc gtgctctatc tgctctaaca acccgacctg ctgggctatc    60
tgcaaaggcg acgtgactgt cgcc    84

<210> SEQ ID NO 32
<211> LENGTH: 78
<212> TYPE: DNA
<213> ORGANISM: Artificial Sequence
<220> FEATURE:
<223> OTHER INFORMATION: primer for G14 peptide insertion

<400> SEQUENCE: 32
gttctcgtcg acaatggctg ctctatctgc tctaacaacc cgacctgctg gctatctgc    60 ggcgacgtga ctgtcgcc    78

<210> SEQ ID NO 33
<211> LENGTH: 72
<212> TYPE: DNA
<213> ORGANISM: Artificial Sequence
<220> FEATURE:
<223> OTHER INFORMATION: primer for G12 peptide insertion

<400> SEQUENCE: 33
gttctcgtcg acaatggctc tatctgctct aacaacccga cctgctgggc tatcggcgac    60
gtgactgtcg cc    72

<210> SEQ ID NO 34
<211> LENGTH: 57
<212> TYPE: DNA
<213> ORGANISM: Artificial Sequence
<220> FEATURE:
<223> OTHER INFORMATION: primer for G7 peptide insertion

<400> SEQUENCE: 34
gttctcgtcg acaatggctg ctctaacaac ccgacctgcg gcgacgtgac tgtcgcc    57

<210> SEQ ID NO 35

<211> LENGTH: 51
<212> TYPE: DNA
<213> ORGANISM: Artificial Sequence
<220> FEATURE:
<223> OTHER INFORMATION: primer for G5 peptide insertion

<400> SEQUENCE: 35
gttctcgtcg acaatggctc taacaacccg accggcgacg tgactgtcgc c        51

<210> SEQ ID NO 36
<211> LENGTH: 50
<212> TYPE: DNA
<213> ORGANISM: Artificial Sequence
<220> FEATURE:
<223> OTHER INFORMATION: MS2 coat protein dna sequence in vicinity of
      AB-loop insertion site for pDSP1

<400> SEQUENCE: 36
cagttcgttc tcgtcgacaa tggcggtacc ggcgacgtga ctgtcgccca         50

<210> SEQ ID NO 37
<211> LENGTH: 27
<212> TYPE: PRT
<213> ORGANISM: Artificial Sequence
<220> FEATURE:
<223> OTHER INFORMATION: RSV F protein "Synagis" epitope. see also SEQ
      ID 5.

<400> SEQUENCE: 37

Leu Thr Asn Ser Glu Leu Leu Ser Leu Ile Asn Asp Met Pro Ile Thr
1               5                   10                  15

Asn Asp Gln Lys Lys Leu Met Ser Asn Asn Val
            20                  25

<210> SEQ ID NO 38
<211> LENGTH: 34
<212> TYPE: PRT
<213> ORGANISM: Artificial Sequence
<220> FEATURE:
<223> OTHER INFORMATION: RSV G protein target region. see also SEQ ID
      20.

<400> SEQUENCE: 38

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn Lys Lys Pro Gly
            20                  25                  30

Lys Lys

<210> SEQ ID NO 39
<211> LENGTH: 18
<212> TYPE: PRT
<213> ORGANISM: Artificial Sequence
<220> FEATURE:
<223> OTHER INFORMATION: p2P7K32 (PP7) (Kpn I site) see also SEQ ID 21.

<400> SEQUENCE: 39

Met Ala Lys Thr Ile Val Leu Ser Val Gly Thr Ala Thr Arg Thr Leu
1               5                   10                  15

Thr Glu

<210> SEQ ID NO 40
<211> LENGTH: 17
<212> TYPE: PRT
<213> ORGANISM: Artificial Sequence

```
<220> FEATURE:
<223> OTHER INFORMATION: pDSP1 (MS2) (Sal1site). See also SEQ ID 22.

<400> SEQUENCE: 40

Ala Asn Phe Thr Gln Phe Val Leu Val Asp Asn Gly Gly Thr Gly Asp
1               5                   10                  15

Val

<210> SEQ ID NO 41
<211> LENGTH: 22
<212> TYPE: PRT
<213> ORGANISM: Artificial Sequence
<220> FEATURE:
<223> OTHER INFORMATION: S10.1 restriction site. See also SEQ ID 23.

<400> SEQUENCE: 41

Val Leu Val Asp Asn Gly Leu Thr Asn Ser Glu Leu Leu Ser Leu Ile
1               5                   10                  15

Gly Asp Val Thr Val Ala
            20

<210> SEQ ID NO 42
<211> LENGTH: 22
<212> TYPE: PRT
<213> ORGANISM: Artificial Sequence
<220> FEATURE:
<223> OTHER INFORMATION: S10.2 restriction site. See also SEQ ID 24.

<400> SEQUENCE: 42

Val Leu Val Asp Asn Gly Ser Glu Leu Leu Ser Leu Ile Asn Asp Met
1               5                   10                  15

Gly Asp Val Thr Val Ala
            20

<210> SEQ ID NO 43
<211> LENGTH: 22
<212> TYPE: PRT
<213> ORGANISM: Artificial Sequence
<220> FEATURE:
<223> OTHER INFORMATION: S10.3 restriction site. see also SEQ ID 25.

<400> SEQUENCE: 43

Val Leu Val Asp Asn Gly Leu Ser Leu Ile Asn Asp Met Pro Ile Thr
1               5                   10                  15

Gly Asp Val Thr Val Ala
            20

<210> SEQ ID NO 44
<211> LENGTH: 22
<212> TYPE: PRT
<213> ORGANISM: Artificial Sequence
<220> FEATURE:
<223> OTHER INFORMATION: S10.4 restriction site. see also SEQ ID 26.

<400> SEQUENCE: 44

Val Leu Val Asp Asn Gly Ile Asn Asp Met Pro Ile Thr Asn Asp Gln
1               5                   10                  15

Gly Asp Val Thr Val Ala
            20

<210> SEQ ID NO 45
<211> LENGTH: 22
<212> TYPE: PRT
<213> ORGANISM: Artificial Sequence
```

```
<220> FEATURE:
<223> OTHER INFORMATION: S10.5 restriction site. see also SEQ ID 27.

<400> SEQUENCE: 45

Val Leu Val Asp Asn Gly Met Pro Ile Thr Asn Asp Gln Lys Lys Leu
1               5                   10                  15

Gly Asp Val Thr Val Ala
            20

<210> SEQ ID NO 46
<211> LENGTH: 22
<212> TYPE: PRT
<213> ORGANISM: Artificial Sequence
<220> FEATURE:
<223> OTHER INFORMATION: S10.6 restriction site. see also SEQ ID 28.

<400> SEQUENCE: 46

Val Leu Val Asp Asn Gly Thr Asn Asp Gln Lys Lys Leu Met Ser Asn
1               5                   10                  15

Gly Asp Val Thr Val Ala
            20

<210> SEQ ID NO 47
<211> LENGTH: 22
<212> TYPE: PRT
<213> ORGANISM: Artificial Sequence
<220> FEATURE:
<223> OTHER INFORMATION: S10.7 restriction site. see also SEQ ID 29.

<400> SEQUENCE: 47

Val Leu Val Asp Asn Gly Asp Gln Lys Lys Leu Met Ser Asn Asn Val
1               5                   10                  15

Gly Asp Val Thr Val Ala
            20

<210> SEQ ID NO 48
<211> LENGTH: 34
<212> TYPE: PRT
<213> ORGANISM: Artificial Sequence
<220> FEATURE:
<223> OTHER INFORMATION: primer for G peptide insertion. see also SEQ ID
      30.

<400> SEQUENCE: 48

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn Lys Lys Pro Gly
            20                  25                  30

Lys Lys

<210> SEQ ID NO 49
<211> LENGTH: 28
<212> TYPE: PRT
<213> ORGANISM: Artificial Sequence
<220> FEATURE:
<223> OTHER INFORMATION: primer for G16 peptide insertion. see also SEQ
      ID 31.

<400> SEQUENCE: 49

Val Leu Val Asp Asn Gly Pro Cys Ser Ile Cys Ser Asn Asn Pro Thr
1               5                   10                  15

Cys Trp Ala Ile Cys Lys Gly Asp Val Thr Val Ala
            20                  25
```

<210> SEQ ID NO 50
<211> LENGTH: 26
<212> TYPE: PRT
<213> ORGANISM: Artificial Sequence
<220> FEATURE:
<223> OTHER INFORMATION: primer for G14 peptide insertion. see also SEQ
      ID 32.

<400> SEQUENCE: 50

Val Leu Val Asp Asn Gly Cys Ser Ile Cys Ser Asn Asn Pro Thr Cys
1               5                   10                  15

Trp Ala Ile Cys Gly Asp Val Thr Val Ala
            20                  25

<210> SEQ ID NO 51
<211> LENGTH: 24
<212> TYPE: PRT
<213> ORGANISM: Artificial Sequence
<220> FEATURE:
<223> OTHER INFORMATION: primer for G12 peptide insertion. see also SEQ
      ID 33.

<400> SEQUENCE: 51

Val Leu Val Asp Asn Gly Ser Ile Cys Ser Asn Asn Pro Thr Cys Trp
1               5                   10                  15

Ala Ile Gly Asp Val Thr Val Ala
            20

<210> SEQ ID NO 52
<211> LENGTH: 19
<212> TYPE: PRT
<213> ORGANISM: Artificial Sequence
<220> FEATURE:
<223> OTHER INFORMATION: primer for G7 peptide insertion. see also SEQ
      ID 34.

<400> SEQUENCE: 52

Val Leu Val Asp Asn Gly Cys Ser Asn Asn Pro Thr Cys Gly Asp Val
1               5                   10                  15

Thr Val Ala

<210> SEQ ID NO 53
<211> LENGTH: 17
<212> TYPE: PRT
<213> ORGANISM: Artificial Sequence
<220> FEATURE:
<223> OTHER INFORMATION: primer for G5 peptide insertion. see also SEQ
      ID 35.

<400> SEQUENCE: 53

Val Leu Val Asp Asn Gly Ser Asn Asn Pro Thr Gly Asp Val Thr Val
1               5                   10                  15

Ala

<210> SEQ ID NO 54
<211> LENGTH: 17
<212> TYPE: PRT
<213> ORGANISM: Artificial Sequence
<220> FEATURE:
<223> OTHER INFORMATION: MS2 coat protein aa sequence in vicinity of
      AB-loop insertion site for pDSP1. see also SEQ ID 36.

```
<400> SEQUENCE: 54

Gln Phe Val Leu Val Asp Asn Gly Gly Thr Gly Asp Val Thr Val Ala
1               5                   10                  15

Pro
```